US008865183B2

(12) United States Patent
Fachinger et al.

(10) Patent No.: US 8,865,183 B2
(45) Date of Patent: Oct. 21, 2014

(54) TREATMENT OF PIGS WITH PCV2 ANTIGENT

(75) Inventors: Vicky Fachinger, Bad Soden (DE); Knut Elbers, Gau Algesheim (DE); Axel Lischewski, Ingelheim am Rhein (DE); Marion Kixmoeller, Munich (DE); Francois-Xavier Orveillon, Mainz (DE); Isabelle Freiin Von Richthofen, Charlottenlund (DK); Michael Piontkowski, Perry, KS (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 249 days.

(21) Appl. No.: 12/519,135

(22) PCT Filed: Dec. 14, 2007

(86) PCT No.: PCT/US2007/087628
§ 371 (c)(1),
(2), (4) Date: Nov. 16, 2009

(87) PCT Pub. No.: WO2008/076915
PCT Pub. Date: Jun. 26, 2008

(65) Prior Publication Data
US 2011/0091499 A1 Apr. 21, 2011

Related U.S. Application Data

(60) Provisional application No. 60/870,311, filed on Dec. 15, 2006.

(51) Int. Cl.
*A61K 39/12* (2006.01)
*A61P 31/20* (2006.01)
*A61K 39/00* (2006.01)

(52) U.S. Cl.
CPC ....... *A61K 39/12* (2013.01); *C12N 2750/10034* (2013.01); *A61K 2039/552* (2013.01)
USPC .................................................. 424/204.1

(58) Field of Classification Search
None
See application file for complete search history.

(56) References Cited

U.S. PATENT DOCUMENTS

| | | | |
|---|---|---|---|
| 5,202,430 A | 4/1993 | Brian et al. | |
| 5,322,774 A | 6/1994 | Peakman et al. | |
| 5,436,001 A | 7/1995 | Kramer | |
| 5,565,205 A | 10/1996 | Petersen et al. | |
| 5,580,557 A | 12/1996 | Kramer | |
| 5,733,555 A | 3/1998 | Chu | |
| 5,885,823 A | 3/1999 | Knittel et al. | |
| 5,925,359 A | 7/1999 | Van Woensel et al. | |
| 5,968,525 A | 10/1999 | Fitzgerald et al. | |
| 6,217,883 B1 | 4/2001 | Allan et al. | |
| 6,287,856 B1 | 9/2001 | Poet et al. | |
| 6,294,176 B1 | 9/2001 | Cochran et al. | |
| 6,368,601 B1 | 4/2002 | Allan et al. | |
| 6,391,314 B1 | 5/2002 | Allan et al. | |
| 6,497,883 B1 | 12/2002 | Bublot et al. | |
| 6,517,843 B1 | 2/2003 | Ellis et al. | |
| 6,660,272 B2 | 12/2003 | Allan et al. | |
| 6,703,023 B1 | 3/2004 | Jestin et al. | |
| 6,794,163 B2 | 9/2004 | Liu et al. | |
| 6,808,900 B2 | 10/2004 | Simonsen | |
| 6,841,364 B2 | 1/2005 | Yuan et al. | |
| 6,846,477 B2 | 1/2005 | Keich et al. | |
| 6,943,152 B1 * | 9/2005 | Audonnet et al. | 514/44 R |
| 6,953,581 B2 | 10/2005 | Allan et al. | |
| 7,018,638 B2 | 3/2006 | Chu et al. | |
| 7,109,025 B1 | 9/2006 | Eloit et al. | |
| 7,122,192 B2 | 10/2006 | Allan et al. | |
| 7,144,698 B2 | 12/2006 | Wang et al. | |
| 7,148,015 B2 | 12/2006 | Jestin et al. | |
| 7,169,394 B2 | 1/2007 | Chu et al. | |
| 7,172,899 B2 | 2/2007 | Liu et al. | |
| 7,179,472 B2 | 2/2007 | Jestin et al. | |
| 7,192,594 B2 | 3/2007 | Haines et al. | |
| 7,211,379 B2 | 5/2007 | Ellis et al. | |
| 7,223,407 B2 | 5/2007 | Jestin et al. | |
| 7,223,594 B2 | 5/2007 | Jestin et al. | |
| 7,244,433 B2 | 7/2007 | Jestin et al. | |
| 7,258,865 B2 | 8/2007 | Jestin et al. | |
| 7,261,898 B2 | 8/2007 | Jestin et al. | |
| 7,273,617 B2 | 9/2007 | Yuan et al. | |
| 7,276,353 B2 | 10/2007 | Meng et al. | |

(Continued)

FOREIGN PATENT DOCUMENTS

| | | | |
|---|---|---|---|
| CA | 2305623 A1 | 4/1999 | |
| CN | 1458167 A | 11/2003 | |

(Continued)

OTHER PUBLICATIONS

Blanchard et al. (Vaccine. 2003; 21: 4565-4575).*
Ellis et al. (Canadian Veterinary Journal. 2001; 42: 461-464).*
Chen et al. (Revue Med. Vet. 2007; 158 (8-9): 458-462).*
Opriessnig et al. (Journal of Swine Health and Production. Jul. and Aug. 2004; (12): 186-191).*
Sequence alignment of SEQ ID No. 11 with UniProt database accession No. 091862 of Meehan et al. entered Nov. 1, 1998.*
Albina et al., "An Experimental Model for Post-weaning Multisystenic Wasting Syndrome (PMWS) in Growing Piglets". 2001, Journal of Comparative Pathology, vol. 123, pp. 292-303.

(Continued)

*Primary Examiner* — Shanon A Foley
(74) *Attorney, Agent, or Firm* — Michael P. Morris; Wendy M. Gombert

(57) ABSTRACT

The present invention relates to a method for the treatment or prophylaxis of a PCV2 infection or for reduction of clinical symptoms caused by or associated with a PCV2 infection in animals a) having anti-PCV2 antibodies and/or b) being young piglets of 1 to 22 days of age, comprising the step of administering an effective amount of a PCV2 antigen to that animal in need of such treatment. Preferably, those animals are pigs or young piglets.

15 Claims, 2 Drawing Sheets

(56) References Cited

U.S. PATENT DOCUMENTS

| | | | |
|---|---|---|---|
| 7,279,166 B2 | 10/2007 | Meng et al. | |
| 7,297,537 B2 | 11/2007 | Jestin et al. | |
| 7,300,785 B2 | 11/2007 | Meerts et al. | |
| 7,312,065 B2 | 12/2007 | Roof et al. | |
| 7,314,628 B2 | 1/2008 | Jestin et al. | |
| 7,323,330 B2 | 1/2008 | Jestin et al. | |
| 7,335,361 B2 | 2/2008 | Liao et al. | |
| 7,358,075 B2 | 4/2008 | Allibert et al. | |
| 7,368,117 B2 | 5/2008 | Fetzer et al. | |
| 7,371,395 B2 | 5/2008 | Parisot et al. | |
| 7,390,494 B2 | 6/2008 | Jestin et al. | |
| 7,405,075 B2 | 7/2008 | Jestin et al. | |
| 7,407,803 B2 | 8/2008 | Jestin et al. | |
| 7,425,444 B2 | 9/2008 | Jestin et al. | |
| 7,700,285 B1 | 4/2010 | Eichmeyer et al. | |
| 7,758,865 B2 | 7/2010 | Jestin et al. | |
| 7,829,101 B2 * | 11/2010 | Eichmeyer et al. | 424/204.1 |
| 7,829,273 B2 * | 11/2010 | Roof et al. | 435/5 |
| 7,829,274 B2 | 11/2010 | Fachinger et al. | |
| 7,833,707 B2 | 11/2010 | Eichmeyer et al. | |
| 7,838,213 B2 * | 11/2010 | Roof et al. | 435/5 |
| 7,838,214 B2 * | 11/2010 | Roof et al. | 435/5 |
| 7,910,306 B2 * | 3/2011 | Eichmeyer et al. | 435/6.14 |
| 7,914,992 B2 | 3/2011 | Fachinger et al. | |
| 7,943,298 B2 | 5/2011 | Fachinger et al. | |
| 7,951,907 B2 | 5/2011 | Jestin et al. | |
| 7,968,285 B2 * | 6/2011 | Roof et al. | 435/5 |
| 8,025,888 B2 | 9/2011 | Eichmeyer et al. | |
| 2002/0146431 A1 | 10/2002 | Allan et al. | |
| 2003/0215455 A1 | 11/2003 | Reynolds et al. | |
| 2004/0062775 A1 | 4/2004 | Jestin et al. | |
| 2004/0076635 A1 | 4/2004 | Jestin et al. | |
| 2004/0091502 A1 | 5/2004 | Jestin et al. | |
| 2005/0008651 A1 | 1/2005 | Jestin et al. | |
| 2005/0013823 A1 | 1/2005 | Keich et al. | |
| 2005/0147966 A1 | 7/2005 | Meng et al. | |
| 2006/0002952 A1 | 1/2006 | Haines et al. | |
| 2006/0029617 A1 | 2/2006 | Charreyre et al. | |
| 2006/0115489 A1 | 6/2006 | Birkett et al. | |
| 2006/0204522 A1 | 9/2006 | Kroll et al. | |
| 2006/0233831 A1 | 10/2006 | Parisot et al. | |
| 2007/0196879 A1 | 8/2007 | Chabriere et al. | |
| 2008/0181910 A1 | 7/2008 | Roof et al. | |
| 2008/0226669 A1 | 9/2008 | Roof et al. | |
| 2008/0233147 A1 | 9/2008 | Jestin et al. | |
| 2008/0267995 A1 | 10/2008 | Roof et al. | |
| 2008/0279889 A1 | 11/2008 | Roof et al. | |
| 2009/0022751 A1 | 1/2009 | Eichmeyer et al. | |
| 2010/0136060 A1 | 6/2010 | Kolb | |
| 2010/0184016 A1 | 7/2010 | Lefebvre et al. | |
| 2010/0189743 A1 | 7/2010 | Jestin et al. | |
| 2011/0033495 A1 | 2/2011 | Roof et al. | |
| 2011/0091449 A1 * | 4/2011 | Payne et al. | 424/131.1 |
| 2011/0091499 A1 * | 4/2011 | Fachinger et al. | 424/204.1 |
| 2011/0217327 A1 * | 9/2011 | Roof et al. | 424/186.1 |
| 2011/0274710 A1 * | 11/2011 | Eichmeyer et al. | 424/186.1 |
| 2013/0273099 A1 | 10/2013 | Fachinger et al. | |
| 2013/0302370 A1 | 11/2013 | Fachinger et al. | |

FOREIGN PATENT DOCUMENTS

| | | |
|---|---|---|
| EP | 1281760 A1 | 2/2003 |
| EP | 1386617 A1 | 2/2004 |
| WO | 8906972 A1 | 8/1989 |
| WO | 9007935 A1 | 7/1990 |
| WO | 9118627 A1 | 12/1991 |
| WO | 9203157 A1 | 3/1992 |
| WO | 9316726 A2 | 9/1993 |
| WO | 9918214 A1 | 4/1999 |
| WO | 9929717 A3 | 6/1999 |
| WO | 9929871 A3 | 6/1999 |
| WO | 0047756 A1 | 8/2000 |
| WO | 0077188 A2 | 12/2000 |
| WO | 0116330 A2 | 3/2001 |
| WO | 0117556 A1 | 3/2001 |
| WO | 0249666 A2 | 6/2002 |
| WO | 03003941 A2 | 1/2003 |
| WO | 2004058142 A2 | 7/2004 |
| WO | 2004069184 A2 | 8/2004 |
| WO | 2005009462 A2 | 2/2005 |
| WO | 2005112995 A1 | 12/2005 |
| WO | 2006072065 A2 | 7/2006 |
| WO | 2006113372 A2 | 10/2006 |
| WO | 2006113373 A2 | 10/2006 |
| WO | 2007028823 A1 | 3/2007 |
| WO | 2007076520 A2 | 7/2007 |
| WO | 2009030684 A2 | 3/2009 |
| WO | 2009103037 A1 | 8/2009 |

OTHER PUBLICATIONS

Allan et al., "Experimental infection of colostrum deprived piglets with porcine circovirus 2 (PCV2) and procine reproductive and respiratory syndrome virus (PRRSV) potentiates PCV2 replication". 2000, Archives of Virology, vol. 145, pp. 2421-2429.

Allan et al., "Letters, Immunostiulations, PCV-2 and PMWS", The Vet. Records, Aug. 5, 2000, pp. 170-171.

Allan et al., "Passive Transfer of Maternal Antibodies to PCV2 Protects Against Development of Post-weaning Multisystemic Wasting Syndrome (PMWS): Experiemental Infections and a Field Study". 2002, The Pig Journal, vol. 50, pp. 59-67.

Allan et al., "PMWS/PCVD: Diagnosis, Disease, and Control: What do we know?" 2006, Proceedings of the 19th IPVS Congress, Copenhagen, Denmark, vol. 1, pp. 1-9.

Allan et al., "Porcine Circoviruses; A Review", J. Vet., Diagn. Invest. 2000, 12, pp. 3-14.

Allan et al., "Reproduction of postweaning multisystemic wasting syndrome in pigs experimentally inoculated with a Swedish porcine circovirus 2 isolate". 2003, Journal of Veterinary Diagnostic Investigation, vol. 15, pp. 553-560.

Allan et al., Guest Editorial, "PCV-2 Infection in Swine; More Than Just Postweaning Multisystemic Wasting Syndrome", The Vet Journ., 2003, 166, pp. 222-223.

Bassaganya-Riera et al., "Conjugated Linoleic Acid Ameliorates Viral Infectivity in a Pig Model of Virally Induced Immunosuppression". 2003, American Society for Nutritional Sciences, pp. 3204-3214.

Boehringer Ingelheim Vetmedica, Inc., "Data from studies consistent with maintaining safety and efficacy of Ingelvac CircoFLEXâ and Ingelvac MycoFLEXâ vaccines when mixed together and administered concurrently to pigs". Feb. 2008, Technical Bulletin, www.bi-vetmedica.com/swine-research/MycoFLEX-Mycoplasma-immunity_TB2.pdf; 14 pages.

Boehringer Ingelheim Vetmedica, Inc., Ingelvacâ Circoflexâ Material Safety Data Sheet, Online Oct. 2006, pp. 1-10, URL:http://bi-vetmedica.com/sites/default/files/ingelvac-circoflex-msds.pdf.

Boisseson et al., "Molecular characterization of Porcine circovirus type 2 isolates from post-weaning multisystemic wasting syndrome-affected and non-affected pigs". 2004, Journal of General Virology, vol. 85, pp. 293-304.

Bolin et al., "Postweaning multisystemic wasting syndrome induced after experimental inoculation of cesarean-derived, colostrum-deprived piglets with type 2 porcine circovirus". 2001, Journal of Veterinary Diagnostic Investigation, vol. 13, pp. 185-194.

Bowie, et al., "Deciphering the Message in Protein Sequences: Tolerance to Amino Acid Substitutions," Science, vol. 247, 1990, pp. 1306-1310.

Caprioli et al., "PCR detection of porcine circovirus type 2 (PCV2) DNA in blood, tonsillar and faecal swabs from experimentally infected pigs". Research in Veterinary Sciences, vol. 81, No. 2, Oct. 2006, pp. 287-292.

Chae, C. "A review of porcine circovirus 2-associated syndromes and diseases". The Veterinary Journal, vol. 169, No. 3, 2005, pp. 326-336.

Chae, C., "Postweaning multisystemic wasting syndrome: a review of aetiology, diagnosis and pathology". 2004, The Veterinary Journal, vol. 168, pp. 41-49.

Charbonneau, G., "Canadian Experiences with Porcine Circovirus Associated Disease". 2007, Iowa Pork Congress; 30 pages.

(56) References Cited

OTHER PUBLICATIONS

Cheung et al., "Kinetics of Porcine jCircovirus Type 2 Replication", Arch Virol., 2002, 147, pp. 43-58.
Chiou, et al., "The Effect of Porcine Circovirus Infection on the Immune Response of Pigs After Vaccination Against Classical Swine Fever and Pseudorabies". 2006, Proceedings of the 19th IPVS Congress, Copenhagen, Denmark, p. 79.
Darwich et al., "Cytokine profiles of peripheral blood mononuclear cells from pigs with postweaning multisystemic wasting syndrome in response to mitogen, superantigen or recall viral antigens". 2003, Journal of General Virology, vol. 84, pp. 3453-3457.
Ellis et al., "Porcine circovirus-2 and concurrent infections in the field". Veterinary Microbiology, vol. 98, No. 2, Feb. 2004, pp. 159-163.
Fachinger et al., "The effect of vaccination against porcine circovirus type 2 in pigs suffering from porcine respiratory disease complex". 2008, Vaccine, vol. 26, pp. 1488-1499.
Fan et al., "Immunogenicity of Empty Capsids of Porcine Circovirus Type 2 Produced in Insect Cells". 2007, Veterinary Research Communications, vol. 31, pp. 487-496.
Fenaux et al., "A Chimeric Porcine Circovirus (PCV) with the Immunogenic Capsid Gene of the Pathogenic PCV Type 2 (PCV2) Clones into the Genomic Backbone of the Nonpathogenic PCV1 Induces Protective Imunity Against PCV2 Infection in Pigs", J. Virol, Jun. 2004, vol. 78, No. 12, pp. 6297-6303.
Gagrcin et al., "Complex of Swine Respiratory Diseases-Strategy of control in light of latest knowledge". Veterinarski Glasnik, vol. 58, No. 7-8, 2004, pp. 409-418.
Genbank Accession No. AAC61738, Version AAC61738.1 GI:3661517, Sep. 29, 1998.
Genbank Accession# AAF87231, PCV2 ORF2 Protein, 2000.
Groner, et al., The Biology of Baculoviruses, vol. 1, Biological Properties and Molecular Biology, 1986, Chapter 9, Specificity and Safety of Baculoviruses, pp. 177-202.
Ha et al., "Outbreak of salmonellosis in pigs with postweaning multisystemic wasting syndrome". Veterinary Record, vol. 156, No. 18, Apr. 2005, pp. 583-584.
International Search Report and Written Opinion for PCT/US2007/087628 mailed Sep. 12, 2008.
Inumaru et al., "Expression of biologically active recombinant porcinee GM-CSF by baculovirus gene expression system". 1998, Immunology and Cell Biology, vol. 76, pp. 195-201.
Jensen et al., "Distinction between Porcine Circovirus Type 2 Enteritis and Porcine Proliferative Enteropathy caused by *Lawsonia intracellularis*". Journal of Comparative Pathology, vol. 135, 2006, pp. 176-182.
Ju et al., "Immunogenicity of a recombinant pseudorabies virus expressing ORF1-ORF2 fusion protein of porcine circovirus type 2". 2005, Veterinary Microbiology, vol. 109, pp. 179-190.
Kamstrup, et al., "Immunisation against PCV2 structural protein by DNA vaccination of mice". 2004, Vaccine, vol. 22, pp. 1358-1361.
Kim et al., "A comparison of the Lymphocyte Subpopulations of Pigs Experimentally Infected with Porcine Circovirus 2 and/or Parvovirus". 2003, The Veterinary Journal, vol. 165, pp. 325-329.
Kim et al., "Association of Porcine Circovirus 2 with Porcine Respiratory Disese Complex", The Vet. Jour., 2003, 166, pp. 251-256.
Kim et al., "Characterization of the Recombinant Proteins of Porcine Circovirus Type2 Field Isolate Expressed in the Baculovirus System". 2002, Journal of Veterinary Science, vol. 3, No. 1, pp. 19-23.
Kim et al., "Enteritis associated with procine circovirus 2 in pigs". 2004, The Canadian Journal of Veterinary Research, vol. 68, pp. 218-221.
Kixmoller et al., "Reduction of PMWS-associated clinical signs and co-infections by vaccination against PCV2". 2008, Vaccine, vol. 26, pp. 3443-3451.
Kost, et al., "Recombinant baculoviruses as mammalian cell gene-delivery vectors". Apr. 2002, Trends in Biotechnology, vol. 20, No. 4, pp. 173-180.
Krakowka et al., "Features of porcine circovirus-2 disease: correlations between lesions, amount and distribution of virus, and clinical outcome". Journal of Veterinary Diagnostic Investigation, vol. 17, No. 3, May 2005, pp. 213-222.
Kyriakis et al., "The Effects of Immuno-modulation of the Clinical and Pathological Expression of Postweaning Multisystemic Wasting Syndrome". 2002, Journal of Comparative Pathology, vol. 126, pp. 38-46.
Ladekjaer-Mikkelsen et al., "Reproduction of postweaning multisystemic wasting syndrome (PMWS) in immunostimulated and non-immunostimulated 3-week-old piglets experimentally infected with prcine circovirus type 2 (PCV2)". 2002, Veterinary Microbiology, vol. 89, pp. 97-114.
Liu et al., "Bacterial Expression of an Immunologically Reactive PCV2 ORF2 Fusion Protein". 2001, Protein Expression and Purification, vol. 21, pp. 115-120.
Liu et al., "Characterization of a Previously Unidentified Viral Protein in Porcine Circovirus Type 2-Infected Cells and Its Role in Virus-Induced Apoptosis". Jul. 2005, Journal of Virology, vol. 79, No. 13, pp. 8262-8274.
MacKinnon, J.D., "Vaccination Ramification? An Objective Look at How Vaccination Might Affect Post-Weaning Multisystemic Wasting Syndrome (PMWS) and Porcine Dermatitis and Nephropathy Syndrome (PDNS)". 2003, The Pig Journal, vol. 51, pp. 36-63.
Mahe et al., "Differential recognition of ORF2 protein from type 1 and type 2 porcine circoviruses and identification of immunorelevant epitopes". 2000, Journal of General virology, vol. 81, pp. 1815-1824.
Maranga et al., "Virus-Like Particle Production at Low Multiplicities of Infection With the Baculovirus Insect Cell System". Aug. 2003, Biotechnology and Bioengineering, vol. 84, No. 2, pp. 246-253.
McNeilly et al., "Evaluation of a Porcine Circovirus Type 2-Specific Antigen-Captive Enzyme-Linked Immunosorbent Assay for the Diagnosis of Postweaning Multisystemic Wasting Syndrome in Pigs: Comparison with Virus Isolation, Immunohistochemistry, and the Polymerase Chain Reaction", J. Vet Diagn. Invest, 2002, 14, pp. 106-112.
Minion et al., "Then Genome Sequence of Mycoplasma hyopneumoniae Strain 232, the Agent of Swine Mycoplasmosis". Nov. 2004, Journal of Bacteriology, vol. 186, No. 21, pp. 7123-7133.
Nawagitgul et al., "Open reading frame 2 of porcine circovirus type 2 encodes a major capsid protein". 2000, Journal of General Virology, vol. 81, pp. 2281-2287.
Nawagitgul et al., Modified Indirect Porcine Circovirus (PCV) Type 2-based and Recombinant Capsid Protein (ORF-2) Based Enzyme-Linked Immunosorbent Assays for Detection of Antibodies to PCV, Clinical and Diagnostic Laboratory Imunology, Ja. 2002, vol. 9, No. 1, pp. 33-40.
Okuda, et al., "Experimental Reproduction of Post-Weaning Multisystemic Wasting Syndrome in Cesarean-Derived, Colostrum-Deprived Piglets Inoculated with Porcine Circovirus Type 2 (PCV2): Investigation of Quantitative PCV2 Distribution and Antibody Responses", J. Vet Diagn. Invest, 2003, 15, pp. 107-114.
Olvera et al., "Comparison of porcine circovirus type 2 load in serum quantified by a real time PCR in postweaning multisystemic wasting syndrome and porcine dermatitis and nephropathy syndrome naturally affected pigs". 2004, Journa of Virological Methods, vol. 117, pp. 75-80.
Opriessnig et al., "Experimental Reproduction of Postweaning Multisystemic Wasting Syndrome in Pigs by Dual Infection with Mycoplasma hyopneumoniae and Porcine Circovirus Type 2". Veterinary Pathology, vol. 41, No. 6, Nov. 2004, pp. 624-640.
Opriessnig et al., "Porcine Circovirus Type 2 Infection Decreases the Efficacy of a Modified Live Porcine Reproductive and Respiratory Syndrome Virus Vaccine", Clinical and Vaccine Immunology, Aug. 2006, vol. 13, No. 8, pp. 923-929.
Ostanello et al., "Experimental infection of 3-week-old conventional colostrum-fed pigs with porcine circovirus type 2 and porcine parvovirus". Veterinary Microbiology, vol. 108, No. 3-4, Jul. 2008, pp. 179-186.
Ponsich, A., "Etude Preliminaire De L'Impact Du Circovac Sur L'infection Par Le PCV2 En Maternite". Nov. 1981.

(56) References Cited

OTHER PUBLICATIONS

Quintana et al., "Clinical and pathological observations on pigs with postweaning multisystemic wasting syndrome". 2001, The Veterinary Record, vol. 149, pp. 357-361.

Rovira et al., "Experimental Inoculation of Conventional Pigs with Porcine Reproductive and Respiratory Syndrome virus and Porcine Circovirus 2", J. Virol, jApr. 2002, vol. 76, No. 7, pp. 3232-3239.

Rueda et al., "Effect of Different Baculovirus Inactivation Procedures on the Integrity and Immunogenicity of Porcine Parvovirus-Like Particles", Vaccine, 2001, 19, pp. 726-734.

Segales et al., "Changes in Peripheral Blood Leukocyte Populations in Pigs with Natural Postweaning Multisystemic Wasting Syndrome (PMWS)", Vet. Immunology & Immunopathology, 2001, 81, pp. 37-44.

Segales et al., "Epidemiology of Porcine Circovirus Type 2 Infection: What do we Know?", Pig News & Information, 2003, vol. 24, No. 4, pp. 103N-110N.

Segales et al., "Postweaning Multisystemic Wasting Syndrome (PMWS) in Pigs, A Review", Vet. Quarterly, 2002, 24(3), pp. 109-124.

Sibila et al., "Use of a Polymerase Chain Reaction Assay and ELISA to Monitor Porcine Circovirus Type 2 Infection in Pigs From Farms with and without Postweaning Multisystemic Wasting jSyndrome", AJVR, Jan. 2004, vol. 65, No. 1, pp. 88-92.

Sorden et al., "Development of a Polyclonal-antibody-based Immunohystochemical Method for the Detection of Type 2 Porcine circovirus in Formalin-Fixed, Paraffin-Embedded Tissue", J. Vet Diagn. Inest, 1999, 11, pp. 528-530.

Vansickle, J., "Circovirus Grips Industry". Jul. 15, 2006, National Hog Farmer.

Vasconcelos et al., "Swine and Poultry Pathogens: the Complete Genome Sequences of Two Strains of Mycoplasma hyopneumoniae and a Strain of Mycoplasma synoviae". Aug. 2005, Journal of Bacteriology, vol. 187, No. 16, pp. 5568-5577.

VIDO Swine Technical Group-Linking Knowledge to practical solutions "Vaccination Guidelines for Swine". Jun. 2004, www.vido.org.

Vincent et al., "Dendritic Cells Harbor Infetious Porcine Circovirus Type 2 in the Abscence of Apparent Cell Modulation or Replication of the Virus". Dec. 2003, Journal of Virology, vol. 77, No. 24, pp. 13288-13300.

Walker, et al., "Development and application of a competitive enzyme-linked immunosorbent assay for the detection of serum antibodies to porcine circovirus type 2". 2000, Journal of Veterinary Diagnostic Investigation, vol. 12, pp. 400-405.

WEB site: "Does stress-free livestock mean safer food?" http://www.foodnavigator.com/Financial-Industry/Does-stress-free-livestock-mean-safer-food Accessed on: Jun. 4, 2004.

Yang, "A Survey on Porcine Circovirus Type 2 Infection and Phylogenetic Analysis of its ORF2 Gene in Hangzhou, Zhejiang Province, CN," J. Zhejiang Univ. Science B, vol. 9(2), 2008, pp. 148-153.

Abstract in English of CN1458167, dated Nov. 26, 2003.

Charbonneau, G., "Canadian Experiences with Porcine Circovirus Associated Disease". 2007, Iowa Pork Congress.

Kim et al., "Efficacy of different disinfectants in vitro against porcine circovirus type 2". The Veterinary Record, vol. 164, May 2009, pp. 599-600.

Riggs et al., "Protective Monoclonal Antibody Defines a Circumsporozoite-Like Glycoprotein Exoantigen of *Cryptosporidium parvum* Sporozoites and Merozoites". The Journal of Immunology, vol. 158, 1997, pp. 1787-1795.

Royer et al., "Susceptibility of porcine circovirus type 2 to commercial and laboratory disinfectants". Journal of Swine Health and Production, vol. 9, No. 6, 2001, pp. 281-284.

Poljak et al., "Spread of porcine circovirus associated disease (PCVAD) in Ontario (Canada) swine herds: Part I. Exploratory spatial analysis". BMC Veterinary Research, vol. 6, No. 59, 2010, pp. 1-15.

Smith et al., "Observations on Experimental Oral Infection with *Salmonella dublin* in Calves and *Salmonella choleraesuis* in Pigs". Journal of Pathology and Bacteriology, vol. 93, No. 1, 1967, pp. 141-156.

Poppe et al., "*Salmonella typhimurium* DT104: A virulent and drug-resistant pathogen". Canadian Veterinary Journal, vol. 39, 1998, pp. 559-565.

Segalés et al., "Postweaning Multisystemic Wasting Syndrome and Porcine Circovirus Ty;e 2: The European Perspective". Trends in Emerging Viral Infections of Swine, Ch. 9.3, PMWS and PCV2: European Perspective, 2002, pp. 297-303.

Fablet et al., "A Case Study of Neonatal Diarrhoea in a Farrow-to-Finish Pig Farm". International Society for Animal Hygiene, Saint Malo, 2004, p. 151.

Dugdale et al., "Immune Response". Medline Plus Medicial Encyclopedia, Updated May 30, 2012, pp. 1-4. [Accessed at http://www.nlm.nih.gov/medlineplus/cncy/article/000821.htm on Mar. 19, 2014].

Fenaux et al., "Immunogenicity and Pathogenicity of Chimeric Infectious DNA Clones of Pathogenic Porcine Circovirus Type 2 (PCV2) and Nonpathogenic PCV1 in Weanling Pigs". Journal of Virology, vol. 77, No. 20, Oct. 2003, pp. 11232-11243.

SEQ ID No. 3 Sequence Alignment with Geneseq Database Accession No. ABV72527 submitted Jan. 2003, in WO2002/077210, 3 pages.

SEQ ID No. 4 Sequence Alignment with Geneseq Database Accession No. ABV72527 submitted Jan. 2003, in WO2002/077210, 3 pages.

SEQ ID No. 5 Sequence Alignment with Geneseq Database Accession No. ABB99415, submitted Jan. 2003 in WO2002/77210, 2 pages.

SEQ ID No. 5 Sequence Alignment with UniProt Database Accession No. Q9YTB6_PCV2 Submitted May 1999 by Fenaux et al. in Journal of Clinical Microbiology, 2000; 38: 2494-2503, 2 pages.

SEQ ID No. 6 Sequence Alignment with UniProt Database Accession No. Q9YTB6_PCV2 Submitted May 1999 by Fenaux et al. in Journal of Clinical Microbiology, 2000; 38: 2494-2503, 2 pages.

SEQ ID No. 6 Sequence Alignment with Geneseq Database Accession No. ADA9081 submitted Nov. 2003 in USPgPUB 2003/096377, 2 pages.

SEQ ID No. 11 Sequence Alignment with Geneseq Database Accession No. AAO23063 submitted Oct. 2003 in WO 2003049703, 2 pages.

* cited by examiner

SEQUENCE LISTING

<160> NUMBER OF SEQ ID NOS: 11

<210> SEQ ID NO 1
<211> LENGTH: 8
<212> TYPE: DNA
<213> ORGANISM: Artificial Sequence
<220> FEATURE:
<223> OTHER INFORMATION: This is a modified Kozak's sequence.

<400> SEQUENCE: 1 ccgccatg                                                                   8

<210> SEQ ID NO 2
<211> LENGTH: 6
<212> TYPE: DNA
<213> ORGANISM: Artificial Sequence
<220> FEATURE:
<223> OTHER INFORMATION: This is a recombinant Eco R1 sequence.

<400> SEQUENCE: 2 gaattc                                                                     6

<210> SEQ ID NO 3
<211> LENGTH: 713
<212> TYPE: DNA
<213> ORGANISM: Porcine circovirus

<400> SEQUENCE: 3
cagctatgac gtatccaagg aggcgttacc gcagaagaag acaccgcccc cgcagccatc          60
ttggccagat cctccgccgc cgcccctggc tcgtccaccc ccgccaccgc taccgttgga         120
gaaggaaaaa tggcatcttc aacacccgcc tctcccgcac cttcggatat actgtggaga         180
aggaaaaatg gcatcttcaa cacccgcctc tcccgcacct tcggatatac tgtgacgact         240
ttgttccccc gggagggggg accaacaaaa tctctatacc ctttgaatac tacagaataa         300
gaaaggttaa ggttgaattc tggccctgct ccccatcac ccagggtgat aggggagtgg          360
gctccactgc tgttattcta gatgataact ttgtaacaaa ggccacagcc ctaacctatg         420
acccatatgt aaactactcc tcccgccata caatccccca accttctcc taccactccc          480
gttacttcac acccaaacct gttcttgact ccactattga ttacttccaa ccaaataaca         540
aaaggaatca gctttggctg aggctacaaa cctctagaaa tgtggaccac gtaggcctcg         600
gcactgcgtt cgaaaacagt aaatacgacc aggactacaa tatccgtgta accatgtatg         660
tacaattcag agaatttaat cttaaagacc ccccacttaa accctaaatg aat                713

<210> SEQ ID NO 4
<211> LENGTH: 713
<212> TYPE: DNA
<213> ORGANISM: Porcine circovirus

<400> SEQUENCE: 4
ccgccatgac gtatccaagg aggcgttacc gcagaagaag acaccgcccc cgcagccatc          60
ttggccagat cctccgccgc cgcccctggc tcgtccaccc ccgccaccgc taccgttgga 120
gaaggaaaaa tggcatcttc aacacccgcc tctcccgcac cttcggatat actgtcaagg 180
ctaccacagt cacaacgccc tcctgggcgg tggacatgat gagatttaat attgacgact 240
ttgttccccc gggagggggg accaacaaaa tctctatacc ctttgaatac tacagaataa 300
gaaaggttaa ggttgaattc tggccctgct cccccatcac ccagggtgat aggggagtgg 360
gctccactgc tgttattcta gatgataact ttgtaacaaa ggccacagcc ctaacctatg 420

```
acccatatgt aaactactcc tcccgccata caatccccca acccttctcc taccactccc    480
gttacttcac acccaaacct gttcttgact ccactattga ttacttccaa ccaaataaca    540
aaaggaatca gctttggctg aggctacaaa cctctagaaa tgtggaccac gtaggcctcg    600
gcactgcgtt cgaaaacagt aaatacgacc aggactacaa tatccgtgta accatgtatg    660
tacaattcag agaatttaat cttaaagacc ccccacttga accctaagaa ttc           713
```

<210> SEQ ID NO 5
<211> LENGTH: 233
<212> TYPE: PRT
<213> ORGANISM: Porcine circovirus

<400> SEQUENCE: 5

```
Met Thr Tyr Pro Arg Arg Arg Tyr Arg Arg Arg His Arg Pro Arg
1               5                   10                  15

Ser His Leu Gly Gln Ile Leu Arg Arg Arg Pro Trp Leu Val His Pro
                20                  25                  30

Arg His Arg Tyr Arg Trp Arg Arg Lys Asn Gly Ile Phe Asn Thr Arg
            35                  40                  45

Leu Ser Arg Thr Phe Gly Tyr Thr Val Lys Ala Thr Thr Val Thr Thr
50                      55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
225                 230
```

<210> SEQ ID NO 6
<211> LENGTH: 233
<212> TYPE: PRT
<213> ORGANISM: Porcine circovirus

<400> SEQUENCE: 6

```
Met Thr Tyr Pro Arg Arg Arg Tyr Arg Arg Arg His Arg Pro Arg
1               5                   10                  15

Ser His Leu Gly Gln Ile Leu Arg Arg Arg Pro Trp Leu Val His Pro
                20                  25                  30

Arg His Arg Tyr Arg Trp Arg Arg Lys Asn Gly Ile Phe Asn Thr Arg
```

```
                   35                  40                  45
Leu Ser Arg Thr Phe Gly Tyr Thr Val Lys Ala Thr Thr Val Thr Thr
 50                  55                  60

Pro Ser Trp Ala Val Asp Met Met Arg Phe Asn Ile Asp Asp Phe Val
 65                  70                  75                  80

Pro Pro Gly Gly Gly Thr Asn Lys Ile Ser Ile Pro Phe Glu Tyr Tyr
                 85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
            115                 120                 125

Phe Val Thr Lys Ala Thr Ala Leu Thr Tyr Asp Pro Tyr Val Asn Tyr
130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
            195                 200                 205

Gln Asp Tyr Asn Ile Arg Val Thr Met Tyr Val Gln Phe Arg Glu Phe
210                 215                 220

Asn Leu Lys Asp Pro Pro Leu Glu Pro
225                 230

<210> SEQ ID NO 7
<211> LENGTH: 756
<212> TYPE: DNA
<213> ORGANISM: Artificial Sequence
<220> FEATURE:
<223> OTHER INFORMATION: This sequence is from porcine circovirus type
      2, open reading frame 2, together with a portion from the pGEM
      T-easy vector.

<400> SEQUENCE: 7
gcggccgcgg gaattcgatc cgccatgacg tatccaagga ggcgttaccg cagaagaaga      60
caccgccccc gcagccatct tggccagatc ctccgccgcc gccccctggct cgtccacccc    120 cgccaccgct accgttggag aaggaaaaat ggcatcttca acacccgcct ctcccgcacc    180
ttcggatata ctgtcaaggc taccacagtc acaacgccct cctgggcggt ggacatgatg    240
agatttaata ttgacgactt tgttcccccg ggaggggggga ccaacaaaat ctctataccc    300
tttgaatact acagaataag aaaggttaag gttgaattct ggccctgctc cccatcacc     360 cagggtgata ggggagtggg ctccactgct gttattctag atgataactt tgtaacaaag    420
gccacagccc taacctatga cccatatgta aactactcct cccgccatac aatcccccaa    480
cccttctcct accactcccg ttacttcaca cccaaacctg ttcttgactc cactattgat    540
tacttccaac caaataacaa aaggaatcag ctttggctga ggctacaaac tctagaaat    600 gtggaccacg taggcctcgg cactgcgttc gaaaacagta atacgacca ggactacaat    660 atccgtgtaa ccatgtatgt acaattcaga gaatttaatc ttaaagaccc ccacttgaa    720 ccctaagaat tctatcacta gtgaattcgc ggccgc                              756

<210> SEQ ID NO 8
<211> LENGTH: 10387
```

<212> TYPE: DNA
<213> ORGANISM: Artificial Sequence
<220> FEATURE:
<223> OTHER INFORMATION: This is the porcine circovirus type 2, ORF-2construct, which includes baculovirus and pGEM T-easy coding
      sequences.

<400> SEQUENCE: 8

```
aagctttact cgtaaagcga gttgaaggat catatttagt tgcgtttatg agataagatt     60
gaaagcacgt gtaaaatgtt tcccgcgcgt tggcacaact atttacaatg cggccaagtt    120
ataaaagatt ctaatctgat atgttttaaa acacctttgc ggcccgagtt gtttgcgtac    180
gtgactagcg aagaagatgt gtggaccgca gaacagatag taaaacaaaa ccctagtatt    240
ggagcaataa tcgatttaac caacacgtct aaatattatg atggtgtgca tttttttgcgg    300 gcgggcctgt tatacaaaaa aattcaagta cctggccaga ctttgccgcc tgaaagcata    360
gttcaagaat ttattgacac ggtaaaagaa tttacagaaa agtgtcccgg catgttggtg    420
ggcgtgcact gcacacacgg tattaatcgc accggttaca tggtgtgcag atatttaatg    480
cacaccctgg gtattgcgcc gcaggaagcc atagatagat tcgaaaaagc cagaggtcac    540
aaaattgaaa gacaaaatta cgttcaagat ttattaattt aattaatatt atttgcattc    600
tttaacaaat actttatcct attttcaaat tgttgcgctt cttccagcga accaaaacta    660
tgcttcgctt gctccgttta gcttgtagcc gatcagtggc gttgttccaa tcgacggtag    720
gattaggccg gatattctcc accacaatgt tggcaacgtt gatgttacgt ttatgctttt    780
ggttttccac gtacgtcttt tggccggtaa tagccgtaaa cgtagtgccg tcgcgcgtca    840
cgcacaacac cggatgtttg cgcttgtccg cggggtattg aaccgcgcga tccgacaaat    900
ccaccacttt ggcaactaaa tcggtgacct gcgcgtcttt tttctgcatt atttcgtctt    960
tcttttgcat ggtttcctgg aagccggtgt acatgcggtt tagatcagtc atgacgcgcg   1020
tgacctgcaa atctttggcc tcgatctgct tgtccttgat ggcaacgatg cgttcaataa   1080
actcttgttt tttaacaagt tcctcggttt tttgcgccac caccgcttgc agcgcgtttg   1140
tgtgctcggt gaatgtcgca atcagcttag tcaccaactg tttgctctcc tcctcccgtt   1200
gtttgatcgc gggatcgtac ttgccggtgc agagcacttg aggaattact tcttctaaaa   1260
gccattcttg taattctatg gcgtaaggca atttggactt cataatcagc tgaatcacgc   1320
cggatttagt aatgagcact gtatgcggct gcaaatacag cgggtcgccc cttttcacga   1380
cgctgttaga ggtagggccc ccattttgga tggtctgctc aaataacgat ttgtatttat   1440
tgtctacatg aacacgtata gctttatcac aaactgtata ttttaaactg ttagcgacgt   1500
ccttggccac gaaccggacc tgttggtcgc gctctagcac gtaccgcagg ttgaacgtat   1560
cttctccaaa tttaaattct ccaattttaa cgcgagccat tttgatacac gtgtgtcgat   1620
tttgcaacaa ctattgtttt ttaacgcaaa ctaaacttat tgtggtaagc aataattaaa   1680
tatgggggaa catgcgccgc tacaacactc gtcgttatga acgcagacgg cgccggtctc   1740
ggcgcaagcg gctaaaacgt gttgcgcgtt caacgcggca aacatcgcaa aagccaatag   1800
tacagttttg atttgcatat taacggcgat tttttaaatt atcttattta ataaatagtt   1860
atgacgccta caactccccg cccgcgttga ctcgctgcac ctcgagcagt tcgttgacgc   1920
cttcctccgt gtggccgaac acgtcgagcg ggtggtcgat gaccagcggc gtgccgcacg   1980
cgacgcacaa gtatctgtac accgaatgat cgtcgggcga aggcacgtcg gcctccaagt   2040
ggcaatattg gcaaattcga aaatatatac agttgggttg tttgcgcata tctatcgtgg   2100
```

```
cgttgggcat gtacgtccga acgttgattt gcatgcaagc cgaaattaaa tcattgcgat    2160
tagtgcgatt aaaacgttgt acatcctcgc ttttaatcat gccgtcgatt aaatcgcgca    2220
atcgagtcaa gtgatcaaag tgtggaataa tgttttcttt gtattcccga gtcaagcgca    2280
gcgcgtattt taacaaacta gccatcttgt aagttagttt catttaatgc aactttatcc    2340
aataatatat tatgtatcgc acgtcaagaa ttaacaatgc gcccgttgtc gcatctcaac    2400
acgactatga tagagatcaa ataaagcgcg aattaaatag cttgcgacgc aacgtgcacg    2460
atctgtgcac gcgttccggc acgagctttg attgtaataa gttttttacga agcgatgaca    2520
tgaccccgt agtgacaacg atcacgccca aagaactgc cgactacaaa attaccgagt       2580
atgtcggtga cgttaaaact attaagccat ccaatcgacc gttagtcgaa tcaggaccgc    2640
tggtgcgaga agccgcgaag tatggcgaat gcatcgtata acgtgtggag tccgctcatt    2700
agagcgtcat gtttagacaa gaaagctaca tatttaattg atcccgatga ttttattgat    2760
aaattgaccc taactccata cacggtattc tacaatggcg gggttttggt caaaatttcc    2820
ggactgcgat tgtacatgct gttaacggct ccgcccacta ttaatgaaat taaaaattcc    2880
aattttaaaa aacgcagcaa gagaaacatt tgtatgaaag aatgcgtaga aggaaagaaa    2940
aatgtcgtcg acatgctgaa caacaagatt aatatgcctc cgtgtataaa aaaaatattg    3000
aacgatttga agaaaacaa tgtaccgcgc ggcggtatgt acaggaagag gtttatacta    3060
aactgttaca ttgcaaacgt ggtttcgtgt gccaagtgtg aaaaccgatg tttaatcaag    3120
gctctgacgc atttctacaa ccacgactcc aagtgtgtgg gtgaagtcat gcatctttta    3180
atcaaatccc aagatgtgta taaaccacca aactgccaaa aatgaaaac tgtcgacaag     3240
ctctgtccgt ttgctggcaa ctgcaagggt ctcaatccta tttgtaatta ttgaataata    3300
aaacaattat aaatgctaaa tttgtttttt attaacgata caaaccaaac gcaacaagaa    3360
catttgtagt attatctata attgaaaacg cgtagttata atcgctgagg taatatttaa    3420
aatcattttc aaatgattca cagttaattt gcgacaatat aatttttattt tcacataaac   3480
tagacgcctt gtcgtcttct tcttcgtatt ccttctcttt ttcattttc tcctcataaa     3540
aattaacata gttattatcg tatccatata tgtatctatc gtatagagta aatttttgt     3600
tgtcataaat atatatgtct ttttttaatgg ggtgtatagt accgctgcgc atagttttc    3660
tgtaatttac aacagtgcta ttttctggta gttcttcgga gtgtgttgct ttaattatta   3720
aatttatata atcaatgaat ttgggatcgt cggttttgta caatatgttg ccggcatagt    3780
acgcagcttc ttctagttca attacaccat ttttttagcag caccggatta acataacttt    3840
ccaaaatgtt gtacgaaccg ttaaacaaaa acagttcacc tccctttttct atactattgt   3900
ctgcgagcag ttgtttgttg ttaaaaataa cagccattgt aatgagacgc acaaactaat    3960
atcacaaact ggaaatgtct atcaatatat agttgctgat atcatggaga taattaaaat    4020
gataaccatc tcgcaaataa ataagtattt tactgttttc gtaacagttt tgtaataaaa    4080
aaacctataa atattccgga ttattcatac cgtcccacca tcgggcgcgg atcagatctg    4140
cagcggccgc gggaattcga tccgccatga cgtatccaag gaggcgttac cgcagaagaa    4200
gacaccgccc ccgcagccat cttggccaga tcctccgccg ccgcccctgg ctcgtccacc    4260
cccgccaccg ctaccgttgg agaaggaaaa atggcatctt caacacccgc ctctcccgca    4320
ccttcggata tactgtcaag gctaccacag tcacaacgcc ctcctgggcg gtggacatga    4380
tgagatttaa tattgacgac tttgttcccc cgggaggggg gaccaacaaa atctctatac    4440
cctttgaata ctacagaata agaaaggtta aggttgaatt ctggccctgc tcccccatca    4500
```

```
cccagggtga tagggagtg ggctccactg ctgttattct agatgataac tttgtaacaa    4560
aggccacagc cctaacctat gacccatatg taaactactc ctcccgccat acaatccccc    4620
aacccttctc ctaccactcc cgttacttca cacccaaacc tgttcttgac tccactattg    4680
attacttcca accaaataac aaaaggaatc agctttggct gaggctacaa acctctagaa    4740
atgtggacca cgtaggcctc ggcactgcgt tcgaaaacag taaatacgac caggactaca    4800
atatccgtgt aaccatgtat gtacaattca gagaatttaa tcttaaagac cccccacttg    4860
aaccctaaga attctatcac tagtgaattc gcggccgccg gccgctccag aattctagaa    4920
ggtacccggg atccttcct gggacccggc aagaaccaaa aactcactct cttcaaggaa    4980
atccgtaatg ttaaacccga cacgatgaag cttgtcgttg gatggaaagg aaaagagttc    5040
tacagggaaa cttggacccg cttcatggaa gacagcttcc ccattgttaa cgaccaagaa    5100
gtgatggatg ttttccttgt tgtcaacatg cgtcccacta gacccaaccg ttgttacaaa    5160
ttcctggccc aacacgctct gcgttgcgac cccgactatg tacctcatga cgtgattagg    5220
atcgtcgagc cttcatgggt gggcagcaac aacgagtacc gcatcagcct ggctaagaag    5280
ggcggcgggt gcccaataat gaaccttcac tctgagtaca ccaactcgtt cgaacagttc    5340
atcgatcgtg tcatctggga gaacttctac aagcccatcg tttacatcgg taccgactct    5400
gctgaagagg aggaaattct ccttgaagtt tccctggtgt tcaaagtaaa ggagtttgca    5460
ccagacgcac ctctgttcac tggtccggcg tattaaaaca cgatacattg ttattagtac    5520
atttattaag cgctagattc tgtgcgttgt tgatttacag acaattgttg tacgtatttt    5580
aataattcat taaatttata atctttaggg tggtatgtta gagcgaaaat caaatgattt    5640
tcagcgtctt tatatctgaa tttaaatatt aaatcctcaa tagatttgta aaataggttt    5700
cgattagttt caaacaaggg ttgttttcc gaaccgatgg ctggactatc taatggattt    5760
tcgctcaacg ccacaaaact tgccaaatct tgtagcagca atctagcttt gtcgatattc    5820
gtttgtgttt tgttttgtaa taaaggttcg acgtcgttca aaatattatg cgcttttgta    5880
tttctttcat cactgtcgtt agtgtacaat tgactcgacg taaacacgtt aaataaagct    5940
tggacatatt taacatcggg cgtgttagct ttattaggcc gattatcgtc gtcgtcccaa    6000
ccctcgtcgt tagaagttgc ttccgaagac gattttgcca tagccacacg acgcctatta    6060
attgtgtcgg ctaacacgtc cgcgatcaaa tttgtagttg agcttttttgg aattatttct    6120 gattgcgggc gttttgggc gggtttcaat ctaactgtgc ccgatttaa ttcagacaac    6180 acgttagaaa gcgatggtgc aggcggtggt aacatttcag acggcaaatc tactaatggc    6240
ggcggtggtg gagctgatga taaatctacc atcggtggag gcgcaggcgg ggctggcggc    6300
ggaggcggag gcggaggtgg tggcggtgat gcagacggcg gtttaggctc aaatgtctct    6360
ttaggcaaca cagtcggcac ctcaactatt gtactggttt cgggcgccgt ttttggtttg    6420
accggtctga cgagtgcg atttttttcg tttctaatag cttccaacaa ttgttgtctg    6480
tcgtctaaag gtgcagcggg ttgaggttcc gtcggcattg gtggagcggg cggcaattca    6540
gacatcgatg gtggtggtgg tggtggaggc gctggaatgt taggcacggg agaaggtggt    6600
ggcggcggtg ccgccggtat aatttgttct ggtttagttt gttcgcgcac gattgtgggc    6660
accggcgcag gcgccgctgg ctgcacaacg gaaggtcgtc tgcttcgagg cagcgcttgg    6720
ggtggtggca attcaatatt ataattggaa tacaaatcgt aaaaatctgc tataagcatt    6780
gtaatttcgc tatcgtttac cgtgccgata tttaacaacc gctcaatgta agcaattgta    6840
```

```
ttgtaaagag attgtctcaa gctcgccgca cgccgataac aagccttttc attttttacta   6900 cagcattgta gtggcgagac acttcgctgt cgtcgacgta catgtatgct tgttgtcaa    6960 aaacgtcgtt ggcaagcttt aaaatattta aagaacatc tctgttcagc accactgtgt    7020
tgtcgtaaat gttgtttttg ataatttgcg cttccgcagt atcgacacgt tcaaaaaatt   7080
gatgcgcatc aattttgttg ttcctattat tgaataaata agattgtaca gattcatatc   7140
tacgattcgt catggccacc acaaatgcta cgctgcaaac gctggtacaa ttttacgaaa    7200
actgcaaaaa cgtcaaaact cggtataaaa taatcaacgg gcgctttggc aaaatatcta   7260
ttttatcgca caagcccact agcaaattgt atttgcagaa acaatttcg gcgcacaatt    7320 ttaacgctga cgaaataaaa gttcaccagt taatgagcga ccacccaaat tttataaaaa   7380
tctattttaa tcacggttcc atcaacaacc aagtgatcgt gatggactac attgactgtc   7440
ccgatttatt tgaaacacta caaattaaag gcgagctttc gtaccaactt gttagcaata   7500
ttattagaca gctgtgtgaa gcgctcaacg atttgcacaa gcacaatttc atacacaacg    7560
acataaaact cgaaaatgtc ttatatttcg aagcacttga tcgcgtgtat gtttgcgatt   7620
acggattgtg caaacacgaa aactcactta gcgtgcacga cggcacgttg gagtatttta    7680
gtccggaaaa aattcgacac acaactatgc acgtttcgtt tgactggtac gcggcgtgtt    7740
aacatacaag ttgctaacgt aatcatggtc atagctgttt cctgtgtgaa attgttatcc    7800
gctcacaatt ccacacaaca tacgagccgg aagcataaag tgtaaagcct ggggtgccta    7860
atgagtgagc taactcacat taattgcgtt gcgctcactg cccgctttcc agtcgggaaa    7920
cctgtcgtgc cagctgcatt aatgaatcgg ccaacgcgcg gggagaggcg gtttgcgtat    7980
tgggcgctct tccgcttcct cgctcactga ctcgctgcgc tcggtcgttc ggctgcggcg    8040
agcggtatca gctcactcaa aggcggtaat acggttatcc acagaatcag gggataacgc    8100
aggaaagaac atgtgagcaa aaggccagca aaaggccagg aaccgtaaaa aggccgcgtt    8160
gctggcgttt ttccataggc tccgcccccc tgacgagcat cacaaaaatc gacgctcaag    8220
tcagaggtgg cgaaacccga caggactata agataccagg cgtttccccc tggaagctc    8280 cctcgtgcgc tctcctgttc cgaccctgcc gcttaccgga tacctgtccg cctttctccc    8340
ttcgggaagc gtggcgcttt ctcatagctc acgctgtagg tatctcagtt cggtgtaggt    8400
cgttcgctcc aagctgggct gtgtgcacga accccccgtt cagcccgacc gctgcgcctt    8460
atccggtaac tatcgtcttg agtccaaccc ggtaagacac gacttatcgc cactggcagc    8520
agccactggt aacaggatta gcagagcgag gtatgtaggc ggtgctacag agttcttgaa    8580
gtggtggcct aactacggct acactagaag gacagtattt ggtatctgcg ctctgctgaa    8640
gccagttacc ttcggaaaaa gagttggtag ctcttgatcc ggcaaacaaa ccaccgctgg    8700
tagcggtggt ttttttgttt gcaagcagca gattacgcgc agaaaaaaag gatctcaaga    8760
agatcctttg atcttttcta cggggtctga cgctcagtgg aacgaaaact cacgttaagg    8820
gattttggtc atgagattat caaaaaggat cttcacctag atcctttta attaaaaatg    8880 aagttttaaa tcaatctaaa gtatatatga gtaaacttgg tctgacagtt accaatgctt    8940
aatcagtgag gcacctatct cagcgatctg tctatttcgt tcatccatag ttgcctgact    9000
ccccgtcgtg tagataacta cgatacggga gggcttacca tctggcccca gtgctgcaat    9060
gataccgcga gacccacgct caccggctcc agatttatca gcaataaacc agccagccgg    9120
aagggccgag cgcagaagtg gtcctgcaac tttatccgcc tccatccagt ctattaattg    9180
ttgccgggaa gctagagtaa gtagttcgcc agttaatagt ttgcgcaacg ttgttgccat    9240
```

-continued

```
tgctacaggc atcgtggtgt cacgctcgtc gtttggtatg gcttcattca gctccggttc    9300
ccaacgatca aggcgagtta catgatcccc catgttgtgc aaaaaagcgg ttagctcctt    9360
cggtcctccg atcgttgtca gaagtaagtt ggccgcagtg ttatcactca tggttatggc    9420
agcactgcat aattctctta ctgtcatgcc atccgtaaga tgcttttctg tgactggtga    9480
gtactcaacc aagtcattct gagaatagtg tatgcggcga ccgagttgct cttgcccggc    9540
gtcaatacgg gataataccg cgccacatag cagaacttta aaagtgctca tcattggaaa    9600
acgttcttcg gggcgaaaac tctcaaggat cttaccgctg ttgagatcca gttcgatgta    9660
acccactcgt gcacccaact gatcttcagc atctttact tcaccagcg tttctgggtg    9720 agcaaaaaca ggaaggcaaa atgccgcaaa aagggaata agggcgacac ggaaatgttg    9780
aatactcata ctcttccttt ttcaatatta ttgaagcatt tatcagggtt attgtctcat    9840
gagcggatac atatttgaat gtatttagaa aaataaacaa ataggggttc cgcgcacatt    9900
tccccgaaaa gtgccacctg acgtctaaga aaccattatt atcatgacat taacctataa    9960
aaataggcgt atcacgaggc cctttcgtct cgcgcgtttc ggtgatgacg gtgaaaacct   10020
ctgacacatg cagctcccgg agacggtcac agcttgtctg taagcggatg ccgggagcag   10080
acaagcccgt cagggcgcgt cagcgggtgt tggcgggtgt cggggctggc ttaactatgc   10140
ggcatcagag cagattgtac tgagagtgca ccatatgcgg tgtgaaatac cgcacagatg   10200
cgtaaggaga aaataccgca tcaggcgcca ttcgccattc aggctgcgca actgttggga   10260
agggcgatcg gtgcgggcct cttcgctatt acgccagctg gcgaaagggg gatgtgctgc   10320
aaggcgatta agttgggtaa cgccagggtt ttcccagtca cgacgttgta aaacgacggc   10380
cagtgcc                                                             10387
```

<210> SEQ ID NO 9
<211> LENGTH: 20
<212> TYPE: PRT
<213> ORGANISM: Porcine circovirus

<400> SEQUENCE: 9

Ser Tyr Pro Arg Arg Tyr Arg Arg Arg His His Pro Pro Ser
1               5                   10                  15

His Leu Gly Gln
            20

<210> SEQ ID NO 10
<211> LENGTH: 19
<212> TYPE: PRT
<213> ORGANISM: Porcine circovirus

<400> SEQUENCE: 10

Pro Arg His His Tyr Arg Pro Arg Arg Lys Asn Gly Ile Phe Asn Thr
1               5                   10                  15

Thr Leu Ser

<210> SEQ ID NO 11
<211> LENGTH: 233
<212> TYPE: PRT
<213> ORGANISM: Artificial Sequence
<220> FEATURE:
<223> OTHER INFORMATION: This is an amino acid sequence for porcine
      circovirus type 2, open reading frame 2.

<400> SEQUENCE: 11

-continued

```
Met Thr Tyr Pro Arg Arg Arg Tyr Arg Arg Arg His Arg Pro Arg
1               5                   10                  15

Ser His Leu Gly Gln Ile Leu Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Arg Thr
    50                  55                  60

Pro Ser Trp Ala Val Asp Met Met Arg Phe Asn Ile Asp Asp Phe Val
65                  70                      75                  80

Pro Pro Gly Gly Gly Thr Asn Lys Ile Ser Ile Pro Phe Glu Tyr Tyr
            85                      90                      95

Arg Ile Lys Lys Val Lys Val Glu Phe Trp Pro Cys Ser Pro Ile Thr
            100                     105                     110

Gln Gly Asp Arg Gly Val Gly Ser Thr Ala Val Ile Leu Asp Asp Asn
            115                     120                     125

Phe Val Thr Lys Ala Thr Ala Leu Thr Tyr Asp Pro Tyr Val Asn Tyr
        130                 135                     140

Ser Ser Arg His Thr Ile Pro Gln Pro Phe Ser Tyr His Ser Arg Tyr
145                     150                     155                 160

Phe Thr Pro Lys Pro Val Leu Asp Ser Thr Ile Asp Tyr Phe Gln Pro
                165                     170                     175

Asn Asn Lys Arg Asn Gln Leu Trp Leu Arg Leu Gln Thr Ser Arg Asn
            180                     185                     190

Val Asp His Val Gly Leu Gly Thr Ala Phe Glu Asn Ser Ile Tyr Asp
        195                     200                     205

Gln Asp Tyr Asn Ile Arg Val Thr Met Tyr Val Gln Phe Arg Glu Phe
    210                     215                     220

Asn Leu Lys Asp Pro Pro Leu Lys Pro
225                 230
```

TREATMENT OF PIGS WITH PCV2 ANTIGENT

RELATED APPLICATIONS

This application is filed under 35 USC 371 from PCT Patent Application No. PCT/US07/87628, which claims the priority benefit of U.S. Application Ser. No. 60/870,311, filed on Dec. 15, 2006, the teachings and content of which are hereby incorporated by reference herein.

SEQUENCE LISTING

This application contains a sequence listing in paper format and in computer readable format, the teachings and content of which are hereby incorporated by reference. The sequence listing is also identical with that incorporated in WO06/072065.

BACKGROUND OF THE INVENTION

1. Field of the Invention

The present invention relates to the use of an immunogenic composition comprising a porcine circovirus type 2 (PCV2) antigen for the prevention, reduction in severity of clinical signs, reduction in the incidence of infection and/or clinical signs, and treatment of several clinical manifestations (diseases) in animals having anti-PCV2 specific antibodies. Preferably, those anti-PCV-2 specific antibodies are maternal antibodies.

2. Description of the Prior Art

Porcine circovirus type 2 (PCV2) is a small (17-22 nm in diameter), icosahedral, non-enveloped DNA virus, which contains a single-stranded circular genome. PCV2 shares approximately 80% sequence identity with porcine circovirus type 1 (PCV1). However, in contrast with PCV1, which is generally non-virulent, infection of swine with PCV2 has recently associated with a number of disease syndromes which have been collectively named Porcine Circovirus-Associated Diseases (PCVAD) (also known as Porcine Circovirus Diseases (PCVD)) (Allan et al, 2006, IPVS Congress). Postweaning Multisystemic Wasting Syndrome (PMWS) is generally regarded to be the major clinical manifestation of PCVAD. (Harding et al., 1997, Swine Health Prod; 5: 201-203; Kennedy et al., 2000, J Comp Pathol; 122: 9-24). PMWS affects pigs between 5-18 weeks of age. PMWS is clinically characterized by wasting, paleness of the skin, unthriftiness, respiratory distress, diarrhea, icterus, and jaundice. In some affected swine, a combination of all symptoms will be apparent while other affected swine will only have one or two of these symptoms. (Muirhead, 2002, Vet. Rec.; 150: 456) During necropsy, microscopic and macroscopic lesions also appear on multiple tissues and organs, with lymphoid organs being the most common site for lesions. (Allan and Ellis, 2000; J Vet. Diagn. Invest., 12: 3-14) A strong correlation has been observed between the amount of PCV2 nucleic acid or antigen and the severity of microscopic lymphoid lesions. Mortality rates for swine infected with PCV2 can approach 80%. In addition to PMWS, PCV2 has been associated with several other infections including pseudorabies, porcine reproductive and respiratory syndrome (PRRS), Glasser's disease, streptococcal meningitis, salmonellosis, postweaning colibacillosis, dietetic hepatosis, and suppurative bronchopneumonia. However, research thus far has not confirmed whether any of these clinical symptoms are in fact, the direct result of a PCV2 infection. Moreover, it is not yet known whether any of these clinical symptoms can be effectively reduced or cured by an active agent directed against PCV2.

Approaches to treat PCV2 infections based on a DNA vaccine are described in U.S. Pat. No. 6,703,023. In WO03/049703 production of a live chimeric vaccine is described, comprising a PCV-1 backbone in which an immunogenic gene of a pathogenic PCV2 strains replaces a gene of the PCV-1 backbone. WO99/18214 has provided several PCV2 strains and procedures for the preparation of a killed PCV2 vaccine. However, no efficacy data have been reported. An effective ORF-2 based subunit vaccine has been reported in WO06/072065 and in WO2007/028823. Any of such vaccines are intended to be used for the vaccination/treatment of swine or pigs older than 3 weeks of age. None of these vaccines have been described for use in young piglets, younger than 3 or 2 weeks of age.

Maternally derived immunity has been shown to confer a certain degree of protection against PCV2 infection and clinical diseases associated with PCV2 infections. This protection has been shown to be titer dependent: higher titers are generally protective whereas lower titers are not (McKeown et al., 2005; Clin. Diagn. Lab. Immunol.; 12: 1347-1351). The mean antibody half-life in weanlings has been estimated to be 19.0 days and the window for PCV2-passive antibody decay within a population is relatively wide (Opriessnig et al. 2004, J. Swine Health Prod. 12:186-191). Low titers of PCV2 passively acquired antibodies present at 10-12 days of age were found to decay by approximately 4.9±1.2 weeks of age, moderate levels of antibodies were found to decay by approximately 8.1±1.9 weeks of age and high levels of antibodies were found to decay by approximately 11.1±2.5 weeks of age (Opriessnig et al., 2006, 37$^{th}$ Annual Meeting of the American Association of Swine Veterinarians). In a timely close correlation with the waning antibody titer stands the occurrence of first clinical signs of PCVAD which occur when piglets are approximately 5 and 12 weeks old (Allan et al, 2000, Vet. Diagn. Investigation, 12: 3-14). Furthermore, PCV2 has also been isolated out of lymphnodes of neonatal piglets (Hirai et al, 2001, Vet. Record; 148:482-484) indicating that even younger piglets may be affected from PCVAD in the absence of protective maternal antibody titers. The obvious correlation between the antibody titer and protection has been proven in a Spanish Field study: Pigs with low antibody titers at 7 weeks of age (mean antibody titer 1:100, range 0 to 1:320) had a significantly higher mortality rate over the following 5 weeks than animals with higher antibody titers (Rodriguez-Arrioja et al., 2002, Am. J. Vet. Res. 63:354-357).

The presence of maternally-derived antibody not only may confer a certain degree of protection against viral infections, which however is not predictable, but also be known to impair the efficacy of immunization. For example higher titers of maternally-derived antibodies to classical swine fever virus (CSFV) inhibit both cell-mediated and humoral immune response to a CSFV vaccine, but lower titers have no significant influence (Suradhat and Damrongwatanapokin, 2003, Vet. Microbiol; 92: 187-194). Also, for live PCV2 vaccines, it has been predicted that they will work most efficiently when given to piglets older than 7 or 8 weeks of age, because the maternal antibodies have mostly waned at that time. Maternal antibody interference is influenced by the type of elicited immune response (Th1 versus Th2) which is dependent (beyond others) on the type of vaccine, type of antigen, type of adjuvant as well as on the amount of administered antigen. Consequently, possible maternal antibody interference may differ for vaccines even if they protect against the same pathogen. Altogether, maternally-derived anti-PCV2 antibodies may confer a certain degree of protection against PCV2, but on the other hand those antibodies may impair the efficacy of any PCV2 vaccine.

The protection of animals by active immunization is further complicated by the fact that a) the time for the decay of maternally derived antibodies (MDA) varies from animal to animal and b) many diseases occur shortly after the decay of antibodies. To face this problem several vaccination strategies foresee a two shot vaccination regime for young animals: The first vaccination is given early in life in order to protect those animals with low MDA. It is accepted that this first vaccination may not be effective in animals with high MDA titers due to an interference with the vaccine antigen. In order to also protect these animals, a second vaccination is required, when high MDA levels are expected to have declined. This kind of vaccination schedule is used for many small animal vaccines (against e.g. canine parvovirosis, canine hepatitis, etc.), equine vaccines (against e.g. equince influenza vaccines) and porcine vaccines (against e.g. *Actinobacillus pleuropneumoniae, Haemophilus parasuis*). As the onset of PCVAD in animals 5 weeks of age or older seems to be linked to the decay of PCV2 antibodies, which is reported to occur in animals aged 4-11 weeks, several vaccine approaches against PCVAD have been described using a two shot vaccination regime in order to circumvent a possible maternal antibody interference. In WO 2007/028823 vaccination of piglets having maternally-derived anti-PCV2 antibodies with more than 20 μg/dose antigen using a two shot vaccination regime is described. Initial vaccination was administered between 1 and 4 weeks of age. All animals were re-vaccinated three weeks after the initial vaccination, when the maternally-derived antibodies in animals with high MDA levels at the time of first vaccination had declined or ceased. Thus, yet no information exist which describes the exact influence of maternally-derived anti-PCV2 antibodies on degree of protection or interference. For that reason, it is recommended not to vaccinate piglets prior to three (3) weeks of age at least with a single shot vaccine regime. Vaccination prior to weeks 3 of age is connected with a certain degree of uncertainty with respect to immunization efficacy. On the other hand, piglets with lower levels of maternally-derived anti-PCV2 antibodies, whereas yet nobody knows what lower levels exactly means, are not sufficiently protected against PCV2 infection prior to week 3 of age. In other words, herds with low MDA titers which are not vaccinated before 3 weeks of age have an immanent risk of PCV2 infections due to lack of a sufficient immune status.

Moreover, such vaccines have not been described to confer protective immunity against PCV2 infection or reducing, lessening the severity of, lessening the incidence of, or curing any clinical symptoms associated therewith in pigs already having anti-PCV2 antibodies, preferably having maternal anti-PC2 antibodies.

DISCLOSURE OF THE INVENTION

Figure 1:
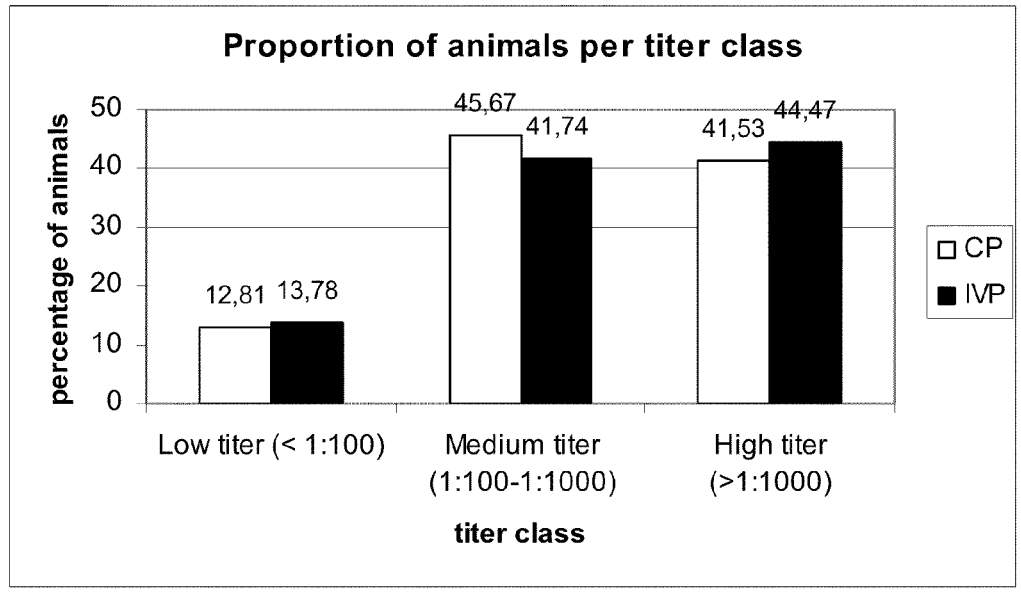
FIG. 1 is a graph of anti-PCV2 antibody titer classes at the time of vaccination.

The present invention overcomes the problems inherent in the prior art and provides a distinct advance in the state of the art. According to general aspect, the present invention provides a method for the treatment or prophylaxis of a PCV2 infection or for reduction of clinical symptoms caused by or associated with a PCV2 infection in animals having anti-PCV2 antibodies, comprising the step of administering an effective amount of PCV2 antigen or an immunogenic composition comprising an PCV2 antigen to that animal in need of such treatment. It was an unpredictable and surprising finding, that the presence of anti-PCV2 antibodies, and in particular of maternal origin, does not impair the efficacy of vaccine comprising PCV2 antigen.

The terms "vaccine" or "immunogenic composition" (both terms are used synonymously) as used herein refer to any pharmaceutical composition containing a PCV2 antigen, which composition can be used to prevent or treat a PCV2 infection-associated disease or condition in a subject. A preferred immunogenic composition can induce, stimulate or enhance the immune response against PCV2. The term thus encompasses both subunit immunogenic compositions, as described below, as well as compositions containing whole killed, or attenuated and/or inactivated PCV2.

Thus according to another aspect, the present invention provides a method for the treatment or prophylaxis of a PCV2 infection or for reduction of clinical symptoms caused by or associated with a PCV2 infection in animals having anti-PCV2 antibodies, in particular maternally-derived anti-PCV2 antibodies, comprising the step of administering an effective amount of PCV2 antigen or an immunogenic composition comprising an PCV2 antigen to that animal in need of such treatment, wherein the immunogenic composition is a subunit immunogenic composition, a compositions containing whole killed, or attenuated and/or inactivated PCV2.

The term "subunit immunogenic composition" as used herein refers to a composition containing at least one immunogenic polypeptide or antigen, but not all antigens, derived from or homologous to an antigen from PCV2. Such a composition is substantially free of intact PCV2. Thus, a "subunit immunogenic composition" is prepared from at least partially purified or fractionated (preferably substantially purified) immunogenic polypeptides from PCV2, or recombinant analogs thereof. A subunit immunogenic composition can comprise the subunit antigen or antigens of interest substantially free of other antigens or polypeptides from PCV2, or in fractionated from. A preferred immunogenic subunit composition comprises the PCV2 ORF-2 protein as described below. Most preferred are immunogenic subunit compositions, which comprise any of the PCV2 antigens provided in WO06/072065, which are all incorporated herein by reference in their entirety.

An "immune response" means but is not limited to the development in a host of a cellular and/or antibody-mediated immune response to the composition or vaccine of interest. Usually, an "immune response" includes but is not limited to one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number or severity of, or lack of one or more of the symptoms associated with PCV2 infections, in delay of onset of viremia, in a reduced viral persistence, in a reduction of the overall viral load and/or a reduction of viral excretion.

The terms "antigen" as used herein refers to an amino acid sequence which elicits an immunological response as described above. An antigen, as used herein, includes the full-length sequence of any PCV2 proteins, analogs thereof, or immunogenic fragments thereof. The term "immunogenic fragment" refers to a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715.

Similarly, conformational epitopes are readily identified by determining spatial conformation of amino acids such as by, e.g., x-ray crystallography and 2-dimensional nuclear magnetic resonance. See, e.g., Epitope Mapping Protocols, supra.

Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; Gardner et al., (1998) 12th World AIDS Conference, Geneva, Switzerland, Jun. 28-Jul. 3, 1998.

According to further aspect, the immunogenic composition as used herein most preferably comprises the polypeptide, or a fragment thereof, expressed by ORF-2 of PCV2. PCV2 ORF-2 DNA and protein, used herein for the preparation of the compositions and within the processes provided herein is a highly conserved domain within PCV2 isolates and thereby, any PCV2 ORF-2 would be effective as the source of the PCV ORF-2 DNA and/or polypeptide as used herein. A preferred PCV2 ORF-2 protein is that of SEQ ID NO: 11 herein and of WO06/072065. A further preferred PCV ORF-2 polypeptide is provided as SEQ ID NO: 5 herein and in WO06/072065. However, it is understood by those of skill in the art that this sequence could vary by as much as 6-10% in sequence homology and still retain the antigenic characteristics that render it useful in immunogenic compositions. The antigenic characteristics of an immunological composition can be, for example, estimated by the challenge experiment as provided by Example 4 of WO06/072065. Moreover, the antigenic characteristic of a modified antigen is still retained, when the modified antigen confers at least 70%, preferably 80%, more preferably 90% of the protective immunity as compared to the PCV2 ORF-2 protein, encoded by the polynucleotide sequence of SEQ ID NO:3 or SEQ ID NO:4 as provided herein and in WO06/072065.

Thus according to a further aspect, the present invention provides a method for the treatment or prophylaxis of a PCV2 infection or for reduction of clinical symptoms caused by or associated with a PCV2 infection in animals having anti-PCV2 antibodies, in particular maternally-derived anti-PCV2 antibodies, comprising the step of administering an effective amount of PCV2 antigen or an immunogenic composition comprising a PCV2 antigen to that animal in need of such treatment, wherein the PCV2 antigen is an antigen of PCV2 ORF-2 protein that has at least 70%, preferably, 80% even more preferably 90% of the protective immunity as compared to compared to the PCV2 ORF-2 protein, encoded by the polynucleotide sequence of SEQ ID NO:3 or SEQ ID NO:4 as provided herein and in WO06/072065. Preferably said PCV2 ORF-2 sequences have the sequence of SEQ ID NO: 11 or SEQ ID NO: 5 as provided herein and in WO06/072065.

In some forms, immunogenic portions of PCV2 ORF-2 protein are used as the antigenic component in the immunogenic composition, comprising PCV2 antigen. The term "immunogenic portion" as used herein refers to truncated and/or substituted forms, or fragments of PCV2 ORF-2 protein and/or polynucleotide, respectively. Preferably, such truncated and/or substituted forms, or fragments will comprise at least 6 contiguous amino acids from the full-length ORF-2 polypeptide. More preferably, the truncated or substituted forms, or fragments will have at least 10, more preferably at least 15, and still more preferably at least 19 contiguous amino acids from the full-length PCV ORF-2 polypeptide. Two preferred sequences in this respect are provided as SEQ ID NO: 9 and SEQ ID NO:10 herein and in WO06/072065. It is further understood that such sequences may be a part of larger fragments or truncated forms.

As mentioned above, a further preferred PCV2 ORF-2 polypeptide is any one encoded by the nucleotide sequences of SEQ ID NO: 3 or SEQ ID NO: 4. However, it is understood by those of skill in the art that this sequence could vary by as much as 6-20% in sequence homology and still retain the antigenic characteristics that render it useful in immunogenic compositions. In some forms, a truncated or substituted form, or fragment of this PCV2 ORF-2 polypeptide is used as the antigenic component in the composition. Preferably, such truncated or substituted forms, or fragments will comprise at least 18 contiguous nucleotides from the full-length PCV2 ORF-2 nucleotide sequence, e.g. of SEQ ID NO: 3 or SEQ ID NO: 4. More preferably, the truncated or substituted forms, or fragments, will have at least 30, more preferably at least 45, and still more preferably at least 57 contiguous nucleotides of the full-length PCV2 ORF-2 nucleotide sequence, e.g. SEQ ID NO: 3 or SEQ ID NO: 4.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, even more preferably 95% of the amino acid residues or nucleotides in the reference sequence must match or comprise a conservative substitution with another amino acid or nucleotide, or a number of amino acids or nucleotides up to 15%, preferably up to 10%, even more preferably up to 5% of the total amino acid residues or nucleotides, not including conservative substitutions, in the reference sequence may be inserted into the reference sequence. Preferably the homolog sequence comprises at least a stretch of 50, even more preferably at least 100, even more preferably at least 250, and even more preferably at least 500 nucleotides.

A "conservative substitution" refers to the substitution of an amino acid residue or nucleotide with another amino acid residue or nucleotide having similar characteristics or properties including size, hydrophobicity, etc., such that the overall functionality does not change significantly.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

Thus, according to a further aspect, the present invention provides a method for the treatment or prophylaxis of a PCV2 infection or for reduction of clinical symptoms caused by or associated with a PCV2 infection in animals having anti-PCV2 antibodies, in particular maternally-derived anti-PCV2 antibodies, comprising the step of administering an effective amount of PCV2 antigen or an immunogenic composition comprising a PCV2 antigen to that animal in need of such treatment, wherein said PCV2 ORF-2 protein is any one of those, described above. Preferably, said PCV2 ORF-2 protein is i) a polypeptide comprising the sequence of SEQ ID NO: 5, SEQ ID NO: 6, SEQ ID NO: 9, SEQ ID NO: 10 or SEQ ID NO: 11 herein or of WO06/07065;

ii) any polypeptide that is at least 80% homologous to the polypeptide of i), iii) any immunogenic portion of the polypeptides of i) and/or ii)

iv) the immunogenic portion of iii), comprising at least 10 contiguous amino acids included in the sequences of SEQ ID NO: 5, SEQ ID NO: 6, SEQ ID NO: 9, SEQ ID NO: 10 or SEQ ID NO: 11 herein or of WO06/072065, v) a polypeptide that is encoded by a DNA comprising the sequence of SEQ ID NO: 3 or SEQ ID NO: 4 herein or of WO06/072065.

vi) any polypeptide that is encoded by a polynucleotide that is at least 80% homologous to the polynucleotide of v), vii) any immunogenic portion of the polypeptides encoded by the polynucleotide of v) and/or vi)

viii) the immunogenic portion of vii), wherein polynucleotide coding for said immunogenic portion comprises at least 30 contiguous nucleotides included in the sequences of SEQ ID NO: 3, or SEQ ID NO: 4 herein or of WO06/072065.

Preferably any of those immunogenic portions have the immunogenic characteristics of PCV2 ORF-2 protein that is encoded by the sequence of SEQ ID NO: 3 or SEQ ID NO: 4 herein or of WO06/07065.

According to a further aspect, PCV2 ORF-2 protein is provided in the immunogenic composition at an antigen inclusion level effective for inducing the desired immune response, namely reducing the incidence of, lessening the severity of, or preventing or reducing one or more clinical symptoms resulting from or associated with a PCV2 infection. Preferably, the PCV2 ORF-2 protein inclusion level is at least 0.2 µg antigen/ml of the final immunogenic composition (µg/ml), more preferably from about 0.2 to about 400 µg/ml, still more preferably from about 0.3 to about 200 µg/ml, even more preferably from about 0.35 to about 100 µg/ml, still more preferably from about 0.4 to about 50 µg/ml, still more preferably from about 0.45 to about 30 µg/ml, still more preferably from about 0.5 to about 18 µg/ml, even more preferably from about 0.6 to about 15 µg/ml even more preferably from about 0.75 to about 8 µg/ml, even more preferably from about 1.0 to about 6 µg/ml, still more preferably from about 1.3 to about 3.0 µg/ml, even more preferably from about 1.4 to about 2.5 µg/ml, even more preferably from about 1.5 to about 2.0 µg/ml, and most preferably about 1.6 µg/ml.

According to a further aspect, the PCV ORF-2 antigen inclusion level is at least 0.2 µg/PCV2 ORF-2 protein as described above per dose of the final antigenic composition (µg/dose), more preferably from about 0.2 to about 400 µg/dose, still more preferably from about 0.3 to about 200 µg/dose, even more preferably from about 0.35 to about 100 µg/dose, still more preferably from about 0.4 to about 50 µg/dose, still more preferably from about 0.45 to about 30 µg/dose, still more preferably from about 0.5 to about 18 µg/dose, even more preferably from about 0.6 to about 15 µg/ml, even more preferably from about 0.75 to about 8 µg/dose, even more preferably from about 1.0 to about 6 µg/dose, still more preferably from about 1.3 to about 3.0 µg/dose, even more preferably from about 1.4 to about 2.5 µg/dose, even more preferably from about 1.5 to about 2.0 µg/dose, and most preferably about 1.6 µg/dose. It has been surprisingly found, that a PCV2 ORF-2 protein inclusion level (antigen content) of less than 20 µg/dose, preferably of about 0.5 to 18 µg/dose is suitable to confer immunity in young animals and/or in animals which are positive for PCV2 antibodies, in particular which are positive for anti-PCV2 maternally-derived antibodies. Thus, according to a further aspect, the present invention provides a method for the treatment or prophylaxis of a PCV2 infection or for reduction of clinical symptoms caused by or associated with a PCV2 infection in animals having anti-PCV2 antibodies, in particular maternally-derived anti-PCV2 antibodies, comprising the step of administering less than 20 µg/dose, preferably of about 0.5 to 18 µg/dose of PCV2 antigen or an immunogenic composition comprising an PCV2 antigen to that animal in need of such treatment. Said PCV2 antigen is any one described in this patent application. Preferably, said PCV2 antigen is any PCV2 ORF-2 protein, more preferably, any PCV2 ORF-2 protein described herein.

The PCV2 ORF-2 polypeptide used in the immunogenic composition in accordance with the present invention can be derived in any fashion including isolation and purification of PCV2 ORF2, standard protein synthesis, and recombinant methodology. Preferred methods for obtaining PCV2 ORF-2 polypeptide are provided in WO06/072065, the teachings and content of which are hereby incorporated by reference in their entirety. Briefly, susceptible cells are infected with a recombinant viral vector containing PCV2 ORF-2 DNA coding sequences, PCV2 ORF-2 polypeptide is expressed by the recombinant virus, and the expressed PCV2 ORF-2 polypeptide is recovered from the supernatant by filtration and inactivated by any conventional method, preferably using binary ethylenimine, which is then neutralized to stop the inactivation process.

The immunogenic composition as used herein also refers to a composition that comprises i) any of the PCV2 ORF-2 protein described above, preferably in concentrations described above, and ii) at least a portion of the viral vector expressing said PCV2 ORF-2 protein, preferably of a recombinant baculovirus. Moreover, the immunogenic composition can comprise i) any of the PCV2 ORF-2 proteins described above, preferably in concentrations described above, ii) at least a portion of the viral vector expressing said PCV2 ORF-2 protein, preferably of a recombinant baculovirus, and iii) a portion of the cell culture supernatant.

Thus, according to a further aspect, the present invention provides a method for the treatment or prophylaxis of a PCV2 infection or for reduction of clinical symptoms caused by or associated with a PCV2 infection in animals having anti-PCV2 antibodies, in particular maternally-derived anti-PCV2 antibodies, comprising the step of administering an effective amount of PCV2 antigen or an immunogenic composition comprising an PCV2 antigen to that animal in need of such treatment, wherein the PCV2 antigen is recombinant PCV2 ORF-2, preferably a baculovirus expressed PCV2 ORF-2. Preferably those recombinant or baculovirus expressed PCV2 ORF-2 having the sequence as described above.

The immunogenic composition as used herein also refers to a composition that comprises i) any of the PCV2 ORF-2 proteins described above, preferably in concentrations described above, ii) at least a portion of the viral vector expressing said PCV2 ORF-2 protein, preferably of a recombinant baculovirus, and iii) a portion of the cell culture; wherein about 90% of the components have a size smaller than 1 µm.

The immunogenic composition as used herein also refers to a composition that comprises i) any of the PCV2 ORF-2 proteins described above, preferably in concentrations described above, ii) at least a portion of the viral vector expressing said PCV2 ORF-2 protein, iii) a portion of the cell culture, iv) and inactivating agent to inactivate the recombinant viral vector preferably BEI, wherein about 90% of the components i) to iii) have a size smaller than 1 µm. Preferably, BEI is present in concentrations effective to inactivate the baculovirus, preferably in an amount of 2 to about 8 mM BEI, preferably of about 5 mM BEI.

The immunogenic composition as used herein also refers to a composition that comprises i) any of the PCV2 ORF-2 proteins described above, preferably in concentrations described above, ii) at least a portion of the viral vector expressing said PCV2 ORF-2 protein, iii) a portion of the cell culture, iv) an inactivating agent to inactivate the recombinant viral vector preferably BEI, and v) a neutralization agent to stop the inactivation mediated by the inactivating agent, wherein about 90% of the components i) to iii) have a size smaller than 1 µm. Preferably, if the inactivating agent is BEI, said composition comprises sodium thiosulfate in equivalent amounts to BEI.

The polypeptide is incorporated into a composition that can be administered to an animal susceptible to PCV2 infection. In preferred forms, the composition may also include additional components known to those of skill in the art (see also Remington's Pharmaceutical Sciences. (1990). 18th ed. Mack Publ., Easton). Additionally, the composition may include one or more veterinary-acceptable carriers. As used herein, "a veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In a preferred embodiment, the immunogenic composition comprises PCV2 ORF-2 protein as provided herewith, preferably in concentrations described above, which is mixed with an adjuvant, preferably Carbopol, and physiological saline.

Those of skill in the art will understand that the composition used herein may incorporate known injectable, physiologically acceptable sterile solutions. For preparing a ready-to-use solution for parenteral injection or infusion, aqueous isotonic solutions, such as e.g. saline or corresponding plasma protein solutions, are readily available. In addition, the immunogenic and vaccine compositions of the present invention can include diluents, isotonic agents, stabilizers, or adjuvants. Diluents can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Adjuvants" as used herein, can include aluminium hydroxide and aluminium phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene oil resulting from theoligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). John Wiley and Sons, NY, pp 51-94 (1995) and Todd et al., Vaccine 15:564-570 (1997).

For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among them, there may be mentioned Carbopol 974P, 934P and 971P. Most preferred is the use of Carbopol, in particular the use of Carbopol 971P, preferably in amounts of about 500 µg to about 5 mg per dose, even more preferred in an amount of about 750 µg to about 2.5 mg per dose and most preferred in an amount of about 1 mg per dose.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from E. coli (recombinant or otherwise), cholera toxin, IMS 1314, or muramyl dipeptide among many others.

Preferably, the adjuvant is added in an amount of about 100 µg to about 10 mg per dose. Even more preferably, the adjuvant is added in an amount of about 100 µg to about 10 mg per dose. Even more preferably, the adjuvant is added in an amount of about 500 µg to about 5 mg per dose. Even more preferably, the adjuvant is added in an amount of about 750 µg to about 2.5 mg per dose. Most preferably, the adjuvant is added in an amount of about 1 mg per dose.

Additionally, the composition can include one or more pharmaceutical-acceptable carriers. As used herein, "a pharmaceutical-acceptable carrier" includes any and all solvents, dispersion media, coatings, stabilizing agents, diluents, preservatives, antibacterial and antifungal agents, isotonic agents, adsorption delaying agents, and the like. Most preferably, the composition provided herewith, contains PCV2 ORF-2 protein recovered from the supernatant of in vitro cultured cells, wherein said cells were infected with a recombinant viral vector containing PCV2 ORF-2 DNA and expressing PCV2 ORF-2 protein, and wherein said cell culture was treated with about 2 to about 8 mM BEI, preferably with about 5 mM BEI to inactivate the viral vector, and an equivalent concentration of a neutralization agent, preferably sodium thiosulfate solution to a final concentration of about 2 to about 8 mM, preferably of about 5 mM.

The present invention also relates to an immunogenic composition that comprises i) any of the PCV2 ORF-2 proteins described above, preferably in concentrations described above, ii) at least a portion of the viral vector expressing said PCV2 ORF-2 protein, iii) a portion of the cell culture, iv) an inactivating agent to inactivate the recombinant viral vector (preferably BEI), and v) a neutralization agent to stop the inactivation mediated by the inactivating agent, preferably sodium thiosulfate in equivalent amounts to BEI; and vi) a suitable adjuvant, preferably Carbopol 971 in amounts described above; wherein about 90% of the components i) to iii) have a size smaller than 1 µm. According to a further aspect, this immunogenic composition further comprises a pharmaceutical acceptable salt, preferably a phosphate salt in physiologically acceptable concentrations. Preferably, the pH of said immunogenic composition is adjusted to a physiological pH, meaning between about 6.5 and 7.5.

The immunogenic composition as used herein also refers to a composition that comprises per one ml i) at least 1.6 µg of PCV2 ORF-2 protein described above, preferably less than 20 µg ii) at least a portion of baculovirus expressing said PCV2 ORF-2 protein iii) a portion of the cell culture, iv) about 2 to 8 mM BEI, v) sodium thiosulfate in equivalent amounts to BEI; and vi) about 1 mg Carbopol 971, and vii)

phosphate salt in a physiologically acceptable concentration; wherein about 90% of the components i) to iii) have a size smaller than 1 μm and the pH of said immunogenic composition is adjusted to about 6.5 to 7.5.

The immunogenic compositions can further include one or more other immuno-modulatory agents such as, e.g., interleukins, interferons, or other cytokines. The immunogenic compositions can also include Gentamicin and Merthiolate. While the amounts and concentrations of adjuvants and additives useful in the context of the present invention can readily be determined by the skilled artisan, the present invention contemplates compositions comprising from about 50 μg to about 2000 μg of adjuvant and preferably about 250 μg/ml dose of the vaccine composition. Thus, the immunogenic composition as used herein also refers to a composition that comprises from about 1 ug/ml to about 60 μg/ml of antibiotics, and more preferably less than about 30 μg/ml of antibiotics.

The immunogenic composition as used herein also refers to a composition that comprises i) any of the PCV2 ORF-2 proteins described above, preferably in concentrations described above, ii) at least a portion of the viral vector expressing said PCV2 ORF-2 protein, iii) a portion of the cell culture, iv) an inactivating agent to inactivate the recombinant viral vector preferably BEI, and v) an neutralization agent to stop the inactivation mediated by the inactivating agent, preferably sodium thiosulfate in equivalent amounts to BEI; vi) a suitable adjuvant, preferably Carbopol 971 in amounts described above; vii) a pharmaceutical acceptable concentration of a saline buffer, preferably of a phosphate salt, and viii) an anti-microbiological active agent; wherein about 90% of the components i) to iii) have a size smaller than 1 μm.

The immunogenic composition as used herein also refers to Ingelvac® CircoFLEX™, (Boehringer Ingelheim Vetmedica Inc, St Joseph, Mo., USA), CircoVac® (Merial SAS, Lyon, France), CircoVent (Intervet Inc., Millsboro, Del., USA), or Suvaxyn PCV-2 One Dose® (Fort Dodge Animal Health, Kansas City, Kans., USA).

Thus according to a further aspect, the present invention provides a method for the treatment or prophylaxis of a PCV2 infection or for reduction of clinical symptoms caused by or associated with a PCV2 infection in animals in animals having anti-PCV2 maternal antibodies, comprising the step of administering an effective amount of a PCV2 antigen to that animal in need of such treatment, wherein the immunogenic composition is CircoFLEX®, CircoVac®, CircoVent or Suvaxyn PCV-2 One Dose®. Most preferably, the immunogenic composition is Ingelvac® CircoFLEX™, and/or the PCV2 antigen is PCV2 ORF-2, preferably, baculovirus expressed PCV2 ORF-2, most preferably as included in Ingelvac® CircoFLEX™.

For investigation of a possible interference of PCV2 antigen with the maternal antibody a study was conducted in which the antibody titers of study animals were determined at the time of vaccination which were then grouped into a low, moderate and high antibody class: Geometric mean titers of <1:100 were considered as low antibody titers, titers of 1:100 to 1:1000 were considered as moderate antibody titers and titers of >1:1000 were considered as high antibody titers. This grouping pattern is comparable to that done in a Canadian field study where antibody titers of 1:80 were considered as low, antibody titers of 1:640 as moderate and antibody titers of >1:1280 as high (Larochelle et al., 2003, Can. J. Vet. Res.; 67: 114-120). In order to analyze the impact of low, medium and high antibody titers at the time of vaccination on viremia, vaccinated and placebo-treated animals were compared with regard to the onset, end, duration of viremia, the number of positive sampling days and the virus load. It was surprisingly found, that the presence of anti-PCV2 antibodies, in particular of maternally-derived antibodies, had no significant impact of any of those parameters. In other words, it was surprisingly found that the efficacy of the PCV2 antigen in prevention and treatment of a PCV2 infection or in reduction of clinical symptoms caused by or associated with a PCV2 infection in animals was not affected at the day of vaccination by the presence of anti-PCV2 antibodies, preferably by anti-PCV2 antibody titers of up to 1:100, preferably of more than 1:100, even more preferably of more than 1:250, even more preferably of more than 1:500, even more preferably of 1:640; even more preferably of more than 1:750, most preferably of more than 1:1000. This effect could be shown in a one shot vaccination experiment, which means that the PCV2 antigen was administered only once and without any subsequent administration of PCV2 antigen.

Methods for detection and quantification of anti-PCV2 antibodies are well known in the art. For example detection and quantification of PCV2 antibodies can be performed by indirect immunofluorescence as described in Magar et al., 2000, Can. J. Vet Res.; 64: 184-186 or Magar et al., 2000, J. Comp. Pathol.; 123: 258-269. Further assays for quantification of anti-PCV2 antibodies are described in Opriessnig et al., 2006, $37^{th}$ Annual Meeting of the American Association of Swine Veterinarians. Moreover, example 2 also describes an indirect immunofluorescence assay that can be used by a person skilled in the art. In cases of controversial results and in any question of doubt, anti-PCV2 titers as mentioned herein, refer to those which are/can be estimated by the assay as described in Example 2.

Thus according to a further aspect, the present invention provides a method for the treatment or prophylaxis of a PCV2 infection or for reduction of clinical symptoms caused by or associated with a PCV2 infection in animals having anti-PCV2 antibodies, in particular maternal antibodies, comprising the step of administering an effective amount of a PCV2 antigen to that animal in need of such treatment, preferably of less than 20 μg/dose wherein said animal has a detectable anti-PCV2 antibody titer of up to 1:100, preferably of more than 1:100, even more preferably of more than 1:250, even more preferably of more than 1:500, even more preferably of 1:640, even more preferably of more than 1:750, most preferably of more than 1:1000. Preferably, such an anti-PCV2 antibody titer is detectable and quantifiable in a specific anti-PCV2 immune assay, preferably in the assay as described in Example 2. More preferably, those anti-PCV-2 antibodies are maternally-derived antibodies. Most preferably, the PCV2 antigen is only administered once, preferably with a dose of less than 20 μg/dose.

Piglets with only low titers (<1:100) or moderate titers (<1:1000) of maternally-derived anti-PCV2 antibodies are not sufficiently protected against PCV2 infections which occur prior to week 3 of age. Therefore, vaccination at a very early stage of life is desirable. Due to the unpredictable and unexpected results provided herein and demonstrating the lack of interference of anti-PCV2 antibodies with PCV2 antigen, vaccination/treatment of animals before 3 weeks of age becomes realistic. Moreover, it has been surprisingly found that anti-PCV2 antibody titers of more than 1:1000 had no influence on the efficacy of the PCV2 vaccine regardless of the level of the existing initial antibody titer. For example, vaccination of high-titer animals (anti-PCV2 antibody titer >1:1000) resulted in a 9.5 day shorter duration of viremia, a 11.9 days earlier end of viremia, 1.9 days less viremic sampling days and an approximately 2-fold reduction of the sum of genomic equivalents/ml as compared to non vaccinated control animals. Upon comparison of vaccinated "high" "moderate" and "low titer animals" no significant differences were observed with regard to the different parameters of PCV2 viraemia. These results indicate that also in the presence of high anti-PCV2 antibody titers, the PCV2 antigen used for vaccination can still significantly reduce viremia in blood (end of viremia, duration of viremia, virus load). In line with this finding, no differences could be found with regard to the live body weight when comparing low and high titer animals of the vaccinated group. Furthermore vaccinated animals with a high anti-PCV2 antibody titer at the time of vaccination/treatment (>1:1000) also showed a significantly higher body weight after the onset of viremia compared to placebo-treated animals with initial high antibody titers (see FIG. 3). Consequently, vaccination/treatment of animals of 1 day of age or older with PCV2 antigen is possible. However, vaccination should be done within the first 8, preferably within the first 7 weeks of age. Thus according to a further aspect, the present invention provides a method for the treatment or prophylaxis of a PCV2 infection or for reduction of clinical symptoms caused by or associated with a PCV2 infection in animals, comprising the step of administering to that animal in need of such treatment at day 1 of age or later, preferably but not later than at week 8 of age an effective amount of a PCV2 antigen. According to a preferred embodiment, less than 20 µg/dose PCV2 antigen are required to confer immunity in such animal. According to a more preferred embodiment, the PCV2 antigen, preferably less than 20 µg/dose thereof is only administered once to the animal in need of such treatment.

According to a further, more general aspect, the present invention provides a method for the treatment or prophylaxis of a PCV2 infection or for reduction of clinical symptoms caused by or associated with a PCV2 infection in young animals, comprising the step of administering an effective amount of a PCV2 antigen to that animal in need of such treatment.

The term "young animal" as used herein refers to an animal of 1 to 22 days of age. Preferably, by the term young animal, an animal of 1 to 20 days of age is meant. More preferably, the term young animal refers to an animal of 1 to 15 days of age, even more preferably of 1 day of age to 14 days of age, even more preferably of 1 to 12 days of age, even more preferably of 1 to 10 days of age, even more preferably of 1 to 8 days of age, even more preferably of 1 to 7 days of age, even more preferably of 1 to 6 days of age, even more preferably of 1 to 5 days of age, even more preferably of 1 to 4 days of age, even more preferably of 1 to 3 days of age, even more preferably of 1 or 2 day(s) of age, and most preferably to an animal of 1 day of age. Thus according to a further aspect, the present invention provides a method for the treatment or prophylaxis of a PCV2 infection or for reduction of clinical symptoms caused by or associated with a PCV2 infection in young animals, comprising the step of administering an effective amount of a PCV2 antigen to an animal of 1 to 22 days of age, preferably of 1 to 20 days of age, more preferably of 1 to 15 days of age, even more preferably of 1 to 14 days of age, even more preferably of 1 to 12 days of age, even more preferably of 1 to 10 days of age, even more preferably of 1 to 8 days of age, even more preferably of 1 to 7 days of age, even more preferably of 1 to 6 days of age, even more preferably of 1 to 5 days of age, even more preferably of 1 to 4 days of age, even more preferably of 1 to 3 days of age, even more preferably of 1 or 2 day(s) of age, most preferably at 1 day of age in need of such treatment. For example, evidence is given that vaccination/treatment on 19 to 22 days of age shows high efficacy of vaccination. Moreover, vaccination/treatment at 12 to 18, preferably 12 to 14 days of age has also be shown to be very effective in the reduction of clinical symptoms associated with PCV2 infections, reduction of overall viral load, reduction of duration of viremia, delay in onset of viremia, and weight gain. Moreover, vaccination at 1 week of age has also been shown to be very effective in reduction of clinical symptoms associated with PCV2 infections, reduction of overall viral load, reduction of duration of viremia, delay in onset of viremia, weight gain. Preferably less than 20 µg/dose PCV2 antigen are required to confer immunity in those young animals. According to more preferred embodiment, the PCV2 antigen, preferably less than 20 µg, is only administered once to that young animal in need of such treatment.

Due to the ubiquity of PCV2 in the field, most of the young piglets are seropositve in respect to PCV2. Thus according to a further aspect, the present invention provides a method for the treatment or prophylaxis of a PCV2 infection or for reduction of clinical symptoms caused by or associated with a PCV2 infection in young animals having anti-PCV2 antibodies at the day of vaccination, comprising the step of administering an effective amount of a PCV2 antigen to an animal of 1 to 22 days of age, preferably of 1 to 20 days of age, more preferably of 1 to 15 days of age, even more preferably of 1 to 14 days of age, even more preferably of 1 to 12 days of age, even more preferably of 1 to 10 days of age, even more preferably of 1 to 8 days of age, even more preferably of 1 to 7 days of age, even more preferably of 1 to 6 days of age, even more preferably of 1 to 5 days of age, even more preferably of 1 to 4 days of age, even more preferably of 1 to 3 days of age, even more preferably at 1 or 2 day(s) of age, and most preferably at 1 day of age in need of such treatment. Preferably, said young animals, at the day of vaccination/treatment, have a detectable anti-PCV2 antibody titer of up to 1:100, preferably of more than 1:100, even more preferably of more than 1:250, even more preferably of more than 1:500, even more preferably of 1:640, even more preferably of more than 1:750, most preferably of more than 1:1000 at the day of vaccination/treatment. Preferably less than 20 µg/dose PCV2 antigen are required to confer a sufficient immunity in those young animals. According to more preferred embodiment, the PCV2 antigen, preferably less than 20 µg, is only administered once to that young animal in need of such treatment.

As described above, vaccination/treatment of young animals with PCV2 antigen resulted in a shortening of viremic phase as compared to non vaccinated control animals. The average shortening time was 9.5 days as compared to non vaccinated control animals of the same species. Therefore, according to a further aspect, the present invention also provides a method for the treatment or prophylaxis of a PCV2 infection or for reduction of clinical symptoms caused by or associated with a PCV2 infection in young animals, comprising the step of administering an effective amount of a PCV2 antigen to that animal in need of such treatment, wherein the treatment or prophylaxis results in shortening of the viremia phase of 5 or more days, preferably 6 or more day, even more preferably of 7 or more days, even more preferably of 8 or more days, even more preferably of 9, even more preferably of 10, even more preferably of 12, even more preferably of 14, and most preferably of more than 16 days as compared to animals of a non-treated control group of the same species. In some cases viremic phase is shortened by more than 20 days. In general, the vaccination of young piglets resulted in a reduction in the loss of weight gain, a shorter duration of viremia, an earlier end to viremia, and a lower virus load. Therefore, according to a further aspect, the present invention provides a method for the treatment or prophylaxis of a PCV2 infection or for reduction of clinical symptoms caused by or associated with a PCV2 infection in young animals, comprising the step of administering an effective amount of a PCV2 antigen to that animal in need of such treatment, wherein said treatment or prophylaxis of PCV2 infection results in an improvement in comparison to animals of a non-treated control group of the same species in a vaccine efficacy parameter selected from the group consisting of a reduction in the loss of weight gain, a shorter duration of viremia, an earlier end to viremia, a lower virus load, or combinations thereof. Preferably less than 20 μg/dose PCV2 antigen are required to cause any of the improved vaccine efficacy parameters mentioned above.

Moreover such improved vaccine efficacy parameter(s) are achieved by a single administration of only one dose.

The term "an effective amount" as used herein means, but is not limited to, an amount of antigen, that elicits or is able to elicit an immune response in an animal, to which said effective dose of PCV2 antigen is administered. Preferably, an effective amount is defined as an amount of antigen that confers a duration of immunity (DOI) of at least 10 weeks, preferably at least 12 weeks, more preferably at least 15 weeks, and most preferably at least 20 weeks.

The amount that is effective depends on the ingredients of the vaccine and the schedule of administration. Typically, when an inactivated virus or a modified live virus preparation is used in the combination vaccine, an amount of the vaccine containing about $10^{2.0}$ to about $10^{9.0}$ TCID$_{50}$ per dose, preferably about $10^{3.0}$ to about $10^{8.0}$ TCID$_{50}$ per dose, and more preferably, about $10^{4.0}$ to about $10^{8.0}$ TCID$_{50}$ per dose is used. In particular, when modified live PCV2 is used in the vaccines, the recommended dose to be administered to the susceptible animal is preferably about $10^{3.0}$ TCID$_{50}$ (tissue culture infective dose 50% end point)/dose to about $10^{6.0}$ TCID$_{50}$/dose and more preferably about $10^{4.0}$ TCID$_{50}$/dose to about $10^{5.0}$ TCID$_{50}$/dose. In general, the quantity of antigen will be between 0.2 and 5000 micrograms, and between $10^{2.0}$ and $10^{9.0}$ TCID$_{50}$, preferably between $10^{3.0}$ and $10^{6.0}$ TCID$_{50}$, more preferably between $10^{4.0}$ and $10^{5.0}$ TCID$_{50}$, when purified antigen is used.

Sub-unit vaccines are normally administered with an antigen inclusion level of at least 0.2 μg antigen per dose, preferably with about 0.2 to about 400 μg/dose, still more preferably with about 0.3 to about 200 μg/dose, even more preferably with about 0.35 to about 100 μg/dose, still more preferably with about 0.4 to about 50 μg/dose, still more preferably with about 0.45 to about 30 μg/dose, still more preferably with about 0.5 to about 18 μg/dose, still more preferably with about 0.6 to about 16 μg/dose, even more preferably with about 0.75 to about 8 μg/dose, even more preferably with about 1.0 to about 6 μg/dose, and still more preferably with about 1.3 to about 3.0 μg/dose.

Unexpectedly, it was found that the prophylactic use of the immunogenic compositions described supra, is effective for the reduction of clinical symptoms caused by or associated with PCV2 infections, preferably in young animals and/or in animals having passive immunity against PCV2 at the day of treatment. In particular, it was discovered that the prophylactic use of the immunogenic compositions as described herein, and specifically of compositions comprising PCV2 ORF-2 antigen, is effective for reducing lymphadenopathy, lymphoid depletion and/or multinucleated/giant histiocytes in animals infected with PCV2 and having maternal anti-PCV-2 antibodies at the day of treatment/vaccination. Furthermore, it was discovered that the prophylactic use of the immunogenic compositions as described herein, and specifically of compositions comprising PCV2 ORF-2 antigen, is effective for reducing (1) interstitial pneumonia with interlobular edema, (2) cutaneous pallor or icterus, (3) mottled atrophic livers, (4) gastric ulcers, (5) nephritis (6) reproductive disorders, e.g. abortion, stillbirths, mummies, etc, (7) Pia like lesions, normally known to be associated with Lawsonia intracellularis infections (Ileitis), (8) lymphadenopathy, (9) lymphoid depletion and/or (10) multinucleated/giant histiocytes (11) Porcine Dermatitis and Nephropathy Syndrome (PDNS), (12) PCVAD associated mortality, (13) PCVAD associated weight loss, (14), reduced growth variability (15), reduced frequency of 'runts' (16), reduced co-infections with Porcine Reproductive and Respiratory Disease Complex (PRRSV). Such an immunogenic composition is also effective in improving economical important growth parameters such as time to slaughter, carcass weight, and/or lean meat ratio. Thus the term "clinical symptoms" as used herein, means, but is not limited to (1) interstitial pneumonia with interlobular edema, (2) cutaneous pallor or icterus, (3) mottled atrophic livers, (4) gastric ulcers, (5) nephritis (6) reproductive disorders, e.g. abortion, stillbirths, mummies, etc, (7) Pia like lesions, normally known to be associated with Lawsonia intracellularis infections (Ileitis), (8) lymphadenopathy, (9) lymphoid depletion and/or (10) multinucleated/giant histiocytes (11) Porcine Dermatitis and Nephropathy Syndrome (PDNS), (12) PCVAD associated mortality, (13) PCVAD associated weight loss, (14) reduced growth variability (15) reduced frequency of 'runts' and (16) reduced co-infections with Porcine Reproductive and Respiratory Disease Complex (PRRSV). Moreover, the antigenic composition described herein reduces the overall circovirus load including a later onset, a shorter duration, an earlier end of viremia, and a reduced viral load and its immunosuppressive impact in young animals, in particular in those having anti-PCV2 antibodies at the day of vaccination, thereby resulting in a higher level of general disease resistance and a reduced incidence of PCV2 associated diseases and symptoms.

Thus, according to a further aspect, the present invention provides a method for the treatment or prophylaxis of a PCV2 infection or for reduction of clinical symptoms caused by or associated with a PCV2 infection in young animals and/or in animals having anti-PCV2 antibodies, comprising the step of administering an effective amount of PCV2 antigen or an immunogenic composition comprising an PCV2 antigen to that animal in need of such treatment, wherein those clinical symptoms are selected from the group consisting of: (1) interstitial pneumonia with interlobular edema, (2) cutaneous pallor or icterus, (3) mottled atrophic livers, (4) gastric ulcers, (5) nephritis (6) reproductive disorders, e.g. abortion, stillbirths, mummies, etc, (7) Pia like lesions, normally known to be associated with Lawsonia intracellularis infections (Ileitis), (8) lymphadenopathy, (9) lymphoid depletion and/or (10) multinucleated/giant histiocytes (11) Porcine Dermatitis and Nephropathy Syndrome (PDNS), (12) PCVAD associated mortality, (13) PCVAD associated weight loss, (14) reduced growth variability (15) reduced frequency of 'runts' and (16) reduced co-infections with Porcine Reproductive and Respiratory Disease Complex (PRRSV). According to a further aspect, the present invention provides a method for the treatment or prophylaxis of a PCV2 infection or for reduction of clinical symptoms caused by or associated with a PCV2 infection in young animals, comprising the step of administering an effective amount of a PCV2 antigen to that animal in need of such treatment, wherein those clinical symptoms are selected from the group consisting of: (1) interstitial pneumonia with interlobular edema, (2) cutaneous pallor or icterus, (3) mottled atrophic livers, (4) gastric ulcers, (5) nephritis (6) reproductive disorders, e.g. abortion, stillbirths, mummies, etc, (7) Pia like lesions, normally known to be associated with Lawsonia intracellularis infections (Ileitis), (8) lymphadenopathy, (9) lymphoid depletion and/or (10) multinucleated/giant histiocytes (11) Porcine Dermatitis and Nephropathy Syndrome (PDNS), (12) PCVAD associated mortality, (13) PCVAD associated weight loss, (14) reduced growth variability (15) reduced frequency of 'runts' and (16) reduced co-infections with Porcine Reproductive and Respiratory Disease Complex (PRRSV).

The composition according to the invention may be administered or applied, orally, intradermally, intratracheally, or intravaginally. The composition preferably may be administered or applied intramuscularly or intranasally, most preferably intramuscularly. In an animal body, it can prove advantageous to apply the pharmaceutical compositions as described above via an intravenous or by direct injection into target tissues. For systemic application, the intravenous, intravascular, intramuscular, intranasal, intraarterial, intraperitoneal, oral, or intrathecal routes are preferred. A more local application can be effected subcutaneously, intradermally, intracutaneously, intracardially, intralobally, intramedullarly, intrapulmonarily or directly in or near the tissue to be treated (connective-, bone-, muscle-, nerve-, epithelial tissue). Depending on the desired duration and effectiveness of the treatment, the compositions according to the invention may be administered once or several times, also intermittently, for instance on a daily basis for several days, weeks or months and in different dosages.

Preferably, one dose of the immunogenic composition as described above is intramuscularly administered to the subject in need thereof. According to a further aspect, the PCV2 antigen or the immunogenic composition comprising any such PCV2 antigen as described herein is bottled in and administered at one (1) mL per dose. Thus, according to a further aspect, the present invention also provides a 1 ml immunogenic composition, comprising PCV-2 antigen as described herein, for the treatment or prophylaxis of a PCV2 infection or for reduction of clinical symptoms caused by or associated with a PCV2 infection in young animals, comprising the step of administering an effective amount of a PCV2 antigen to that animal in need of such treatment. According to a further aspect, the present invention also provides a 1 ml immunogenic composition, comprising PCV-2 antigen as described herein, treatment or prophylaxis of a PCV2 infection or for reduction of clinical symptoms caused by or associated with a PCV2 infection in animals having anti-PCV2 antibodies, comprising the step of administering an effective amount of PCV2 antigen or an immunogenic composition comprising an PCV2 antigen to that animal in need of such treatment.

According to a further aspect, at least one further administration of at least one dose of the immunogenic composition as described above is given to a subject in need thereof, wherein the second or any further administration is given at least 14 days beyond the initial or any former administrations. Preferably, the immunogenic composition is administered with an immune stimulant. Preferably, said immune stimulant is given at least twice. Preferably, at least 3 days, more preferably at least 5 days, even more preferably at least 7 days are in between the first and the second or any further administration of the immune stimulant. Preferably, the immune stimulant is given at least 10 days, preferably 15 days, even more preferably 20, and even more preferably at least 22 days beyond the initial administration of the immunogenic composition provided herein. A preferred immune stimulant is, for example, keyhole limpet hemocyanin (KLH), preferably emulsified with incomplete Freund's adjuvant (KLH/ICFA). However, it is herewith understood, that any other immune stimulant known to a person skilled in the art can also be used. The term "immune stimulant" as used herein, means any agent or composition that can trigger the immune response, preferably without initiating or increasing a specific immune response, for example the immune response against a specific pathogen. It is further instructed to administer the immune stimulant in a suitable dose.

The "animal" as used herein means swine, pig or piglet.

DETAILED DESCRIPTION OF THE PREFERRED EMBODIMENTS

The following examples set forth preferred materials and procedures in accordance with the present invention. Although any methods and materials similar or equivalent to those described herein can be used in the practice or testing of the present invention, the preferred methods, devices, and materials are now described. It is to be understood, however, that these examples are provided by way of illustration only, and nothing therein should be deemed a limitation upon the overall scope of the invention.

EXAMPLE 1

Preparation of PCV2 ORF-2 Antigen

Initial SF+ cell cultures from liquid nitrogen storage were grown in Excell 420 media (JRH Biosciences, Inc., Lenexa, Kans.) in suspension in sterile spinner flasks with constant agitation. The cultures were grown in 100 mL to 250 mL spinner flasks with 25 to 150 mL of Excell 420 serum-free media. When the cells had multiplied to a cell density of $1.0$-$8.0 \times 10^6$ cells/mL, they were split to new vessels with a planting density of $0.5$-$1.5 \times 10^6$ cells/mL. Subsequent expansion cultures were grown in spinner flasks up to 36 liters in size or in stainless steel bioreactors of up to 300 liters for a period of 2-7 days at 25-29° C.

After seeding, the flasks were incubated at 27° C. for four hours. Subsequently, each flask was seeded with a recombinant baculovirus containing the PCV2 ORF-2 gene (SEQ ID NO: 4). The recombinant baculovirus containing the PCV2 ORF-2 gene was generated as described in WO06/072065. After being seeded with the baculovirus, the flasks were then incubated at 27±2° C. for 7 days and were also agitated at 100 rpm during that time. The flasks used ventilated caps to allow for air flow.

After incubation, the resulting supernatant were harvested, filtered in order to remove cell debris and inactivated. The supernatant was inactivated by bringing its temperature to 37±2° C. and binary ethylenimine (BEI) is added to the supernatant to a final concentration of 5 mM. The samples were then stirred continuously for 72 to 96 hrs. A 1.0 M sodium thiosulfate solution to give a final minimum concentration of 5 mM was added to neutralize any residual BEI. After inactivation, PCV2 ORF-2 buffered with phosphate buffer and Carpopol was added to about 0.5 to 2.5 mg/dose. The final dose comprises about 16 µg PCV2 ORF-2 antigen.

EXAMPLE 2

Anti PCV-2 Immuno Assay

PK15 (e.g. ATCC CCL-33) or VIDO R1 cells described in WO 02/07721, are seeded onto a 96 well plate (about 20.000 to 60.000 cells per wells). Cells are infected with a PCV2 isolate, when monolayers are approximately 65 to 85% confluent. Infected cells are incubated for 48 hours. Medium is removed and wells are washed 2 times with PBS. The wash buffer is discarded and cells are treated with cold 50/50 methanol/acetone fixative (~100 μl/well) for about 15 min at about −20° C. The fixative is discarded and the plates are air tried. Serial dilutions of porcine serum samples are prepared in PBS, added to the plates and incubated to allow antibodies to bind if present in the serum samples for about 1 hr at 36.5±1° C. In addition, serial dilutions of an anti-PCV2 positive and negative control sample (Positive Control and Negative Control Samples) are run in parallel. The plates are then washed three times with PBS. The PBS is discarded. Plates are then stained with an commercial Goat anti-Swine FITC conjugate diluted 1:100 in PBS and incubated for about 1 hr at 36.5±1° C., which allows detection of antibodies bound to infected cells. After incubation is complete, the microplates are removed from incubator, the conjugate is discarded and the plates are washed 2 times with PBS. The plates were read using UV microscopy and individual wells reported as positive or negative. The Positive Control and Negative Control samples are used to monitor the test system. If the controls are within expected ranges the test results are acceptable in regard to test method parameters. The serum antibody titers were calculated using the highest dilution showing specific IFA reactivity and the number of wells positive per dilution, or a 50% endpoint is calculated using the appropriate Reed-Muench formula.

EXAMPLE 3

Efficacy of PCV2 ORF-2 (Ingelvac® CircoFLEX™) in Young Animals Having Low or High Anti-PCV2 Antibodies For investigation of a possible interference of the vaccine with the maternal antibody a study was conducted in which the antibody titers of all study animals were determined at the time of vaccination which were then grouped into a low, moderate and high antibody class: Geometric mean titers of <1:100 were considered as low antibody titers, titers of 1:100 to 1:1000 were considered as moderate antibody titers and titers of >1:1000 were considered as high antibody titers.

Study Performance

Approximately 500 animals were included into the study. The study animals were balanced and equally distributed among both treatment groups with regard to initial body weight and litter assignment. At 20 days of age all study animals received a single dose (1 ml) of the PCV2 vaccine (Investigational Veterinary Product, IVP) or a single (1 ml) dose of a placebo containing adjuvanted cell culture supernatant (Control Product, CP) by intramuscular injection in the right side of the neck. Study animals were followed until the end of fattening. Blood samples from all study animals were collected and subsequently analyzed by IFAT in order to determine the antibody titers at the time of vaccination. Following this, the initial antibody titers were correlated with the weight gain. In addition, dependent on the initial antibody titer, animals were grouped into three classes (low, moderate and high initial antibody titers) and 'high titer' animals of both treatment groups were then compared for possible differences with regard to weight gain and viremia.

Results

Initial Antibody Titers

At the time of vaccination the majority of animals had either moderate antibody titers (defined as 1:100 to 1:1000) or high antibody titers (defined as >1:1000). Only approximately 13% percent of animals had low antibody titers (defined as <1:100). Due to the absence of PCV2 infection at the time of study initiation it can be concluded that the antibody titers on study day 0 were possibly maternally derived. No significant differences in the antibody titers of study day 0 were observed between the two treatment groups. An overview about the percentage of animals per titer class is given in FIG. 1.

Correlation of Antibody Titers at the Time of Vaccination with Viremia in Blood

In order to determine whether a high antibody titer at the time of vaccination (>1:1000) had an impact on viremia, vaccinated and placebo-treated animals with high initial antibody titers were compared with regard to the onset, end, duration of viremia, the number of positive sampling days and the virus load. Table 1 summarizes the comparison of viremia parameters of the 'high-titer animals' from both treatment groups.

TABLE 1

Comparison of viremia in 'high titer animals' from both treatment groups

| Investigated Parameter | Treatment Group | Number of pigs | Mean | Median | P |
|---|---|---|---|---|---|
| Onset of Viremia | CP | 38 | 111.90 days | 113.00 days | 0.7843 |
|  | IVP | 36 | 109.50 days | 113.00 days | ns |
|  | CP − IVP |  | 2.4 days |  |  |
| Duration of Viremia | CP | 38 | 27.00 days | 27.50 days | <0.0001 |
|  | IVP | 36 | 17.50 days | 6.50 days | *** |
|  | CP − IVP |  | 9.50 days |  |  |
| End of Viremia | CP | 38 | 138.90 days | 141.00 days | 0.0033 |
|  | IVP | 36 | 127.00 days | 122.50 days | ** |
|  | CP − IVP |  | 11.9 days |  |  |
| Positive Sampling days | CP | 39 | 3.70 days | 3.00 days | 0.0082 |
|  | IVP | 47 | 1.80 days | 1.00 days | ** |
|  | CP − IVP |  | 1.9 days |  |  |
| Mean Sum gE (log10) | CP | 39 | 18.79 gE | 17.21 gE | <0.0001 |
|  | IVP | 47 | 9.12 gE | 5.38 gE | *** |
|  | CP − IVP |  | 9.67 gE |  |  | gE: sum of genomic equivalents per ml
P: p-value of the Wilcoxon Mann-Whitney test for comparisons between groups;
ns: not significant, p > 0.05;
** significant, p ≤ 0.01;
*** significant, p < 0.001

Compared to the placbebo-treated high-titer animals, vaccinated high-titer animals had a 9.5 day shorter duration of viremia, a 11.9 days earlier end of viremia, 1.9 days less viremic sampling days and an approximately 2-fold reduction of the sum of genomic equivalents/ml over the course of the study. These results indicate that also in the presence of high maternal antibody titers the IVP can still significantly reduce viremia in blood (end of viremia, duration of viremia, virus load).

Correlation of Antibody Titers at the Time of Vaccination with Weight Gain

It was next investigated, whether the initial antibody titer had any effect on the weight gain over the course of the study. Table 2 presents the correlation of the initial antibody titer with the weight gain at different time intervals as determined by the calculation of the Spearman rank coefficient and the p-value.

A statistically significant negative correlation between the antibody titer and the weight gain was found for both treatment groups at study weeks 0 to 7 indicating that a high maternal antibody titer negatively influences the weight gain development in the rearing phase. No other statistically significant correlations between the initial antibody titer and the weight gain during different time intervals were observed. It can therefore be concluded that the level of maternal antibody titer did not have an influence on the weight gain from 10 weeks of age (study week 7) onwards for neither the vaccinated or for the placebo-treated animals.

TABLE 2

Correlation of the PCV2 antibody titer at the time of vaccination with body weight gain over the course of the study

Figure 2:
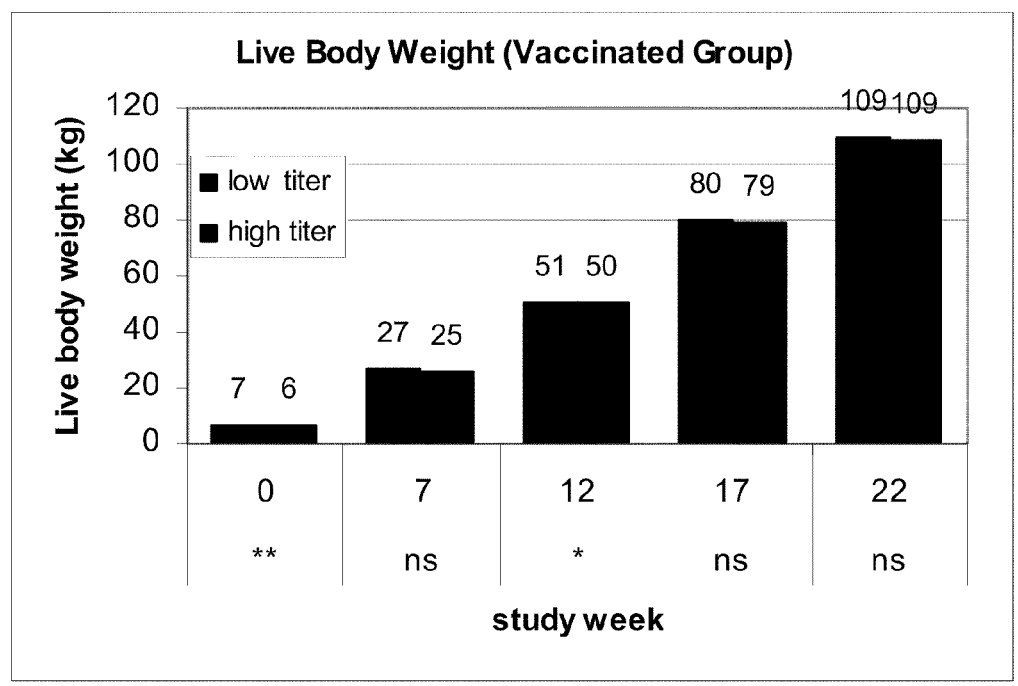
FIG. 2 is a graph comparing the live body weight in vaccinated animals with low (<1:100) and high (>1:1000) anti-PCV2 antibodies.

| | | Correlation of antibody titer at the time of vaccination with weight gain | | | |
|---|---|---|---|---|---|
| | | Study week 0-7 | Study week 7-12 | Study week 12-17 | Study week 17-22 |
| CP | r | −0.09623 | 0.03501 | −0.00521 | −0.02774 |
| | P | 0.0086** | 0.3425 ns | 0.8884 ns | 0.4617 ns |
| | n | 744 | 737 | 728 | 706 |
| IVP | r | −0.09748 | 0.04309 | −0.00954 | 0.02694 |
| | P | 0.0077** | 0.2440 ns | 0.7974 ns | 0.4710 ns |
| | n | 746 | 733 | 727 | 718 | r: Spearman rank correlation coefficient
P: p-value of test on r = 0:
ns: not significant, p > 0.05;
**significant, $p \leq 0.01$
n: Number of animals In line with this finding, no differences could be found with regard to the live body weight when comparing low and high titer animals of the vaccinated group. FIG. 2 shows that the body weight after the onset of viremia (study week 17 and 22) was comparable irrespective of the level of initial antibody titer (FIG. 2).

Figure 3:
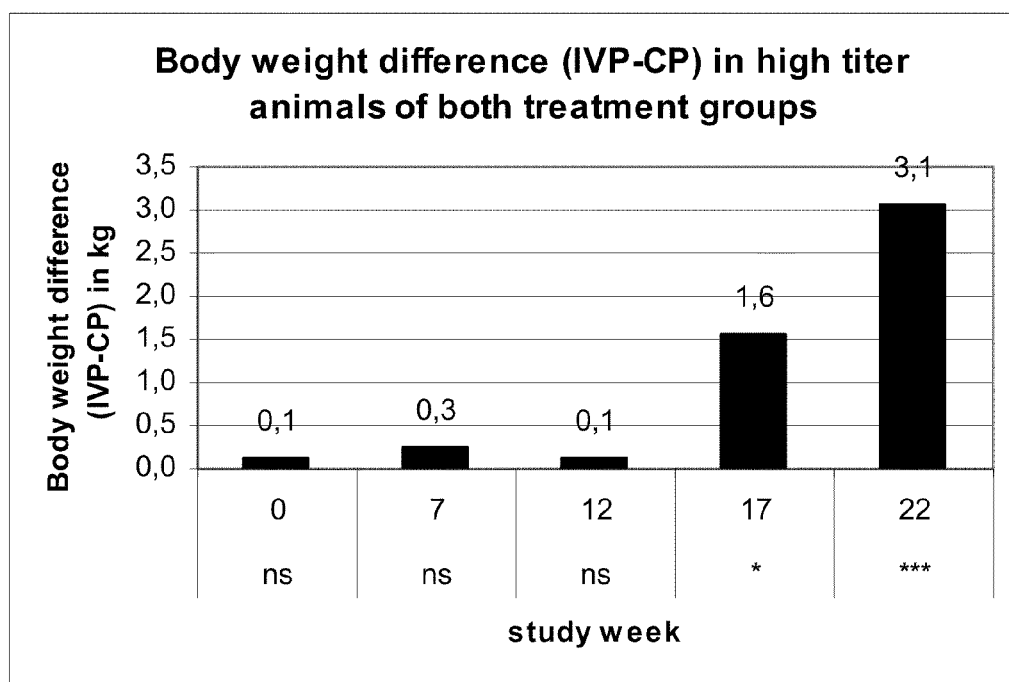
FIG. 3 is a graph illustrating body weight difference in vaccinated (IVP) as compared to placebo-treated control animals (CP).

Furthermore vaccinated animals with a high antibody titer at the time of vaccination (>1:1000) also showed a significantly higher body weight after the onset of viremia compared to placebo-treated animals with initial high antibody titers. As can be seen in FIG. 3 the body weight (LSMean) at study week 17 and at study week 22 was indeed significantly higher in vaccinated 'high titer animals' (study week 17: 1.55 kg, p=0.0328; study week 22: 3.06 kg, p=0.0007) than in placebo-treated 'high titer animals'. Together these findings demonstrate that there is no interference of the IVP with the antibody titer at the time of vaccination.

Conclusion

For analysis of a possible maternal antibody interference the initial antibody titer was correlated with the two efficacy parameters viremia in blood and live body weight. Compared to the placebo-treated 'high titer animals' the following statistical significant findings were noted for the vaccinated 'high titer animals':
reduction in loss of weight gain
shorter duration of viremia and earlier end of viremia
lower virus load

EXAMPLE 4

Efficacy of PCV2 ORF-2 (Ingelvac® CircoFLEX™) in Young Animals Having Anti-PCV2 Antibodies with Respect to Lymphoid Depletion, Lymphoid Inflammation, and Lymphoid Immunohistochemistry (IHC)

The objective of this blinded vaccination-challenge study was to evaluate at what age pigs vaccinated with Porcine Circovirus Vaccine, Type 2, Killed Baculovirus Vector established immunity in the presence of Porcine Circovirus Type 2 (PCV2) maternally-derived antibodies. Three primary parameters were analyzed following challenge. These three parameters included lymphoid depletion, lymphoid inflammation, and lymphoid immunohistochemistry (IHC). To demonstrate immunity in the presence of PCV2 maternally-derived antibodies, conventionally raised pigs vaccinated with PCV2 vaccine at 3 weeks of age or at 8 weeks of age, must demonstrate statistically significant differences (p<0.05) for lymphoid depletion, lymphoid inflammation, and lymphoid IHC, compared with challenge control pigs treated with Control Product at 3 weeks of age.

Study Performance

One hundred twenty (120) conventionally raised pigs, 21 days of age on Day 0 (D0), were assigned completely at random to one of five treatment groups. On D0, blood samples were collected from all pigs, Group 1a was treated with Investigational Veterinary Product (IVP; PCV2 reference vaccine) at 3 weeks of age.

Group 1b was treated with Investigational Veterinary Product (IVP; PCV2 reference vaccine) at 8 weeks of age.

Group 2 was treated with Control Product (CP) at 3 weeks of age.

Pigs were observed for clinical assessments post-vaccination from D-1 to D59. Additional pre-challenge blood samples were collected on D14, D28, D42, D56 and D63. A summary of Group PCV2 serological Geometric Mean Titers (GMT) pre-challenge are shown below in Table 3.

TABLE 3

Group PCV2 Serological Geometric Mean Titers Pre-challenge

| Group - | PCV2 Serology - GMT | | | | | |
|---|---|---|---|---|---|---|
| Treatment | D0 | D14 | D28 | D42 | D 6 | D63 |
| Group 1a IVP administered 3 weeks of age | 556.5 | 252.8 | 142.0 | 56.2 | 32.0 | 51.3 |
| Group 1b IVP administered at 8 weeks of age | 476.2 | 308.2 | 151.6 | 36.2 | 29.3 | 48.3 |
| Group 2 CP administered at 3 weeks of age | 513.8 | 310.7 | 134.3 | 36.9 | 16.9 | 24.5 |

All remaining pigs received 2.0 mL of keyhole limpet hemocyanin (KLH) emulsified in incomplete Freund's adjuvant (ICFA) IM on D60 (Day Post-Challenge (DPC)-3) and D66 (DPC 3). On D63 (DPC 0), remaining pigs received 1.0 mL of PCV2 Iowa State University Veterinary Diagnostic Laboratory (ISUVDL) challenge material (4.75 $\log_{10}$ TCID$_{50}$/mL) IM and 1.0 mL of the same material IN. Body weights, rectal temperatures, clinical observations, blood samples and nasal swabs were collected on the day of challenge and periodically post-challenge. At necropsy for each pig, gross lesions were noted and lung and lymphoid tissue samples were collected. Lung and lymphoid tissues were examined microscopically by ISUVDL for lesions and for the presence of PCV2 antigen by IHC testing. A general description of the challenge phase of the study is shown below in table 4.

TABLE 4

Challenge Phase of Study

| Group - Treatment | Number | KLH/ICFA On D60 (DPC −3) | PCV2 Challenge on D63 (DPC 0) | KLH/ICFA On D66 (DPC 3) | Day of Necropsy |
|---|---|---|---|---|---|
| Group 1a IVP administered 3 weeks of age | 20 | Yes | Yes | Yes | D87 (DPC 24) or D88 (DPC 25) |
| Group 1b IVP administered at 8 weeks of age | 21 | Yes | Yes | Yes | D87 (DPC 24) or D88 (DPC 25) |
| Group 2 CP administered at 3 weeks of age | 20 | Yes | Yes | Yes | D87 (DPC 24) or D88 (DPC 25) |

On D86, the geometric mean titers were 906.6, 2447.1, 2014.9, respectively.

Results

Following PCV2 challenge exposure on D63 and subsequent necropsy, Group 1a had a statistically significant lower proportion of pigs positive for lymphoid depletion (p=0.0084), a lower proportion of pigs positive for lymphoid inflammation (p=0.0079), and a lower proportion of pigs with IHC lymphoid-positive tissues (p=0.0031), all in comparison to Group 2. Following PCV2 challenge, Group 1b had a statistically significant lower proportion of pigs positive for lymphoid depletion (p=0.0148), a lower proportion of pigs positive for lymphoid inflammation (p=0.0036), and a lower proportion of pigs with IHC lymphoid-positive tissues (p=0.0013), all in comparison to Group 2. A summary of primary efficacy parameter results for Groups 1a, 1b and 2 are shown below in table 5.

There were significant differences between Groups 1a and 1b compared with Group 2 for microscopic lung inflammation (p≤0.0407), but no significant differences between these groups for lung tissue testing positive for PCV2 antigen by IHC testing (p≥0.2317). There were no significant differences between Groups 1a and 1b compared with Group 2 for clinical assessments post-vaccination, ADG, clinical signs post-challenge, pyrexia, nasal shedding of PCV2, % total lung scores and lymphadenopathy.

In conclusion, Group 1a, vaccinated at 3 weeks of age and having a GMT of 556.6 at the time of vaccination, was significantly protected from lymphoid depletion, lymphoid inflammation, and lymphoid tissues testing positive for PCV2 antigen by IHC testing, compared with Group 2. Group 1b, vaccinated at 8 weeks of age and having a GMT of 151.6 one week prior to vaccination, was significantly protected from lymphoid depletion, lymphoid inflammation and lymphoid tissues testing positive for PCV2 antigen by IHC testing, compared with Group 2. Pigs with PCV2 maternally-derived antibodies were protected from Porcine Circovirus Associated Disease (PCVAD) when vaccinated as early as 3 weeks of age.

TABLE 5

Summary of Primary Efficacy Parameter Results for Groups 1a and 1b compared with Group 2

| Group - Treatment | PCV2 Serological status on Day 0 | Lymphoid Depletion (+/total) | Lymphoid Inflammation (+/total) | Lymphoid IHC (+/total) |
|---|---|---|---|---|
| Group 1a IVP at 3 weeks of age | Seropositive | 1/20 (5%) *p = 0.0084 | 3/20 (15%) *p = 0.0079 | 3/20 (15%) *p = 0.0031 |
| Group 1b IVP at 8 weeks of age | Seropositive | 2/21 (9.5%) *p = 0.0148 | 3/21 (14.3%) *p = 0.0036 | 3/21 (14.3%) *p = 0.0013 |
| Group 2 CP at 3 weeks of age | Seropositive | 9/20 (45%) | 12/20 (60%) | 13/20 (65%) |

*p value compared with Group 2 - Fisher's Exact Test

We claim:

1. A method for the prophylaxis of PCV2 infection in a pig in need thereof or for the reduction of clinical symptoms caused by or associated with a PCV2 infection in a pig in need thereof, wherein the pig has maternal anti-PCV2 antibodies and is 1 to 20 days of age, the method comprising the step of:
administering a single dose of an effective amount of a PCV2 ORF2 protein to a pig in need thereof, wherein the PCV2 ORF2 protein has at least 90% sequence homology with SEQ ID NO. 11 and wherein the prophylaxis of PCV2 infection or the reduction of clinical symptoms caused by or associated with a PCV2 infection occurs after the single dose of PCV2 ORF2 protein.

2. The method according to claim 1, wherein the animals having anti-PCV-2 antibodies have an anti-PCV2 antibody titre of more than 1:100 in a PCV specific immunoassay.

3. The method according to claim 2, wherein the animals have the anti-PCV2 antibody titre at the time the PCV2 antigen is administered.

4. The method according to claim 1, wherein the animals having anti-PCV-2 antibodies have an anti-PCV2 antibody titre of more than 1:1000 in a PCV specific immunoassay.

5. The method according to claim 1, wherein the PCV2 ORF2 protein is administered at day 7 of age or later.

6. The method according to claim 1, wherein the PCV-2 ORF2 protein is administered at day 14 of age or later.

7. The method according to claim 1, wherein the treatment or prophylaxis results in shortening of the viremia phase of 5 or more days as compared to pigs of a non-treated control group.

8. The method according to claim 1, wherein the PCV-2 ORF2 protein is expressed by a recombinant baculovirus prior to administration.

9. The method according to claim 1, wherein the PCV2 ORF2 protein is Ingelvac® CircoFLEX®.

10. The method according to claim 1, wherein 0.5 to 18 µg/dose of said PCV2 ORF2 protein is administered to the pig in need of such treatment.

11. The method according to claim 1, wherein the prophylaxis of PCV2 infection results in an improvement in comparison to animals of a non-treated control group in a vaccine efficacy parameter selected from the group consisting of a reduction in the loss of weight gain, a shorter duration of viremia, an earlier end to viremia, a lower virus load, or combinations thereof.

12. A method for the prophylaxis of a PCV2 infection or for the reduction of clinical symptoms caused by PCV2 infection of piglets between 1 and 20 days of age that are PCV2 maternally derived antibody positive against PCV2 infection, comprising administering a single dose of a vaccine composition comprising at least 0.2 µg PCV2 ORF2 protein to a piglet in need thereof wherein the prophylaxis of PCV2 infection or the reduction of clinical symptoms caused by or associated with a PCV2 infection occurs after the single dose of PCV2 ORF2 protein.

13. The method of claim 12, wherein the amount of PCV2 ORF2 protein is 0.5 μg to 18 μg.

14. The method of claim 12, wherein the vaccine composition is effective for the protection of the piglets after a single dose thereof.

15. A method for the prophylaxis of PCV2 infection in a pig in need thereof or for the reduction of clinical symptoms caused by or associated with a PCV2 infection in a pig in need thereof, wherein the pig has anti-PCV2 maternal antibodies and is 1 to 20 days of age, the method comprising the step of:
  administering a single dose of 0.5 to 18 μg/dose of PCV2 ORF2 protein to a pig in need thereof, wherein the PCV2 ORF2 protein has at least 90% sequence homology with SEQ ID NO. 11 and wherein the prophylaxis of PCV2 infection or the reduction of clinical symptoms caused by or associated with a PCV2 infection occurs after the single dose of PCV2 ORF2 protein.

* * * * *